United States Patent
Wang et al.

(10) Patent No.: US 10,183,915 B2
(45) Date of Patent: Jan. 22, 2019

(54) AXIALLY CHIRAL ISOMERS, AND PREPARATION METHODS THEREFOR AND PHARMACEUTICAL USES THEREOF

(71) Applicant: MEDSHINE DISCOVERY INC., Jiangsu (CN)

(72) Inventors: Jianfei Wang, Jiangsu (CN); Jing Zhang, Jiangsu (CN); Long Zhang, Jiangsu (CN); Yang Zhang, Jiangsu (CN); Jian Li, Jiangsu (CN); Shuhui Chen, Jiangsu (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 15/563,132

(22) PCT Filed: Apr. 1, 2016

(86) PCT No.: PCT/CN2016/078239
§ 371 (c)(1),
(2) Date: Sep. 29, 2017

(87) PCT Pub. No.: WO2016/155653
PCT Pub. Date: Oct. 6, 2016

(65) Prior Publication Data
US 2018/0079731 A1 Mar. 22, 2018

(30) Foreign Application Priority Data

Apr. 3, 2015 (CN) .......................... 2015 1 0159331
May 12, 2015 (CN) .......................... 2015 1 0241034

(51) Int. Cl.
C07D 249/12 (2006.01)
A61K 31/4196 (2006.01)

(52) U.S. Cl.
CPC ........ *C07D 249/12* (2013.01); *A61K 31/4196* (2013.01); *C07B 2200/07* (2013.01); *Y02P 20/544* (2015.11)

(58) Field of Classification Search
CPC .......................... C07D 249/12; C07B 2200/07
USPC ........................................................ 514/384
See application file for complete search history.

(56) References Cited

U.S. PATENT DOCUMENTS

| 8,084,483 B2 * | 12/2011 | Quart .................. | C07D 249/12 514/383 |
|---|---|---|---|
| 8,754,118 B2 | 6/2014 | Aoki et al. | |
| 2014/0024696 A1 | 1/2014 | Aoki et al. | |

FOREIGN PATENT DOCUMENTS

| CN | 101679243 A | 3/2010 |
|---|---|---|
| CN | 101918377 A | 12/2010 |
| CN | 102093343 A | 6/2011 |
| CN | 103524440 A | 1/2014 |
| CN | 105399694 A | 3/2016 |
| CN | 105622531 A | 6/2016 |
| TW | 201639823 A | 11/2016 |
| WO | 2009070740 A2 | 6/2009 |
| WO | 2011085009 A2 | 7/2011 |
| WO | 2011126852 A2 | 10/2011 |
| WO | 2011159732 A1 | 12/2011 |
| WO | 2012050589 A1 | 4/2012 |
| WO | 2012092395 A2 | 7/2012 |
| WO | 2014008295 A1 | 1/2014 |
| WO | 2014198241 A1 | 12/2014 |
| WO | 2017147270 A1 | 8/2017 |

OTHER PUBLICATIONS

PCT International Search Report and Written Opinion dated Jul. 7, 2016 from corresponding Application No. PCT/CN2016/078239, 14 pages.
T.S. M. Berge et al.,—Pharmaceutical Salts-Journal of Pharmaceutical Sciences 1977, 66 pp. 1-19.
Remington The Science and Practice of Pharmacy, 21st Ed Lippincott Williams and Wilkins 2005, Chapters 37-39, pp. 702-775.
Remington The Science and Practice of Pharmacy, 21st Ed Lippincott Williams and Wilkins 2005, Chapters 40-43, pp. 776-870.
Remington The Science and Practice of Pharmacy, 21st Ed Lippincott Williams and Wilkins 2005, Chapters 44-47, pp. 871-964.
Remington The Science and Practice of Pharmacy, 21st Ed Lippincott Williams and Wilkins 2005, Chapters 48-54, pp. 965-1057.
Jun. 27, 2016 International Search Report issued in International Patent Application No. PCT/CN2016/078239.
Dec. 8, 2017 Extended European Search Report (EESR) issued in the counterpart Europe patent application of International Patent Application No. PCT/CN2016/078239.
Laplante et al—Assessing atropisomer axial chirality in Drug Discovery and Development. Journal of Medicinal Chemistry, 2011, pp. 7005-7022.
CHMP Assessment Report: Zurampic Dec. 17, 2015.
Barrett et al—Spontaneous transfer of chirality in an atropisomerically enriched two-axis system, Nature, 2014, pp. 71-75.
Jianfei Wang et al—Discovery and Assessment of Astropisomers of ()-Lesinurad, ACS Medicinal Chemistry Letters, 2017, pp. 299-303.

\* cited by examiner

*Primary Examiner* — Kristin A Vajda
(74) *Attorney, Agent, or Firm* — Dilworth IP, LLC

(57) ABSTRACT

Disclosed are two axially chiral isomers and pharmaceutically available salts thereof, preparation method therefor, and pharmaceutical use of the two axially chiral isomers or pharmaceutical compositions thereof.

20 Claims, 3 Drawing Sheets

AXIALLY CHIRAL ISOMERS, AND PREPARATION METHODS THEREFOR AND PHARMACEUTICAL USES THEREOF

FIELD OF THE PRESENT INVENTION

The present invention relates to two axially chiral isomers and pharmaceutically available salts thereof, preparation method therefor, and pharmaceutical use of the two axially chiral isomers or pharmaceutical compositions thereof.

BACKGROUND OF THE PRESENT INVENTION

Lesinurad (CAS: 878672-00-5, RDEA594), as a urate-lowering agent, was firstly reported by Ardea Biosciences Inc. in patent application (WO2009070740), the synthetic route thereof was shown as below.

Synthetic Route 1:

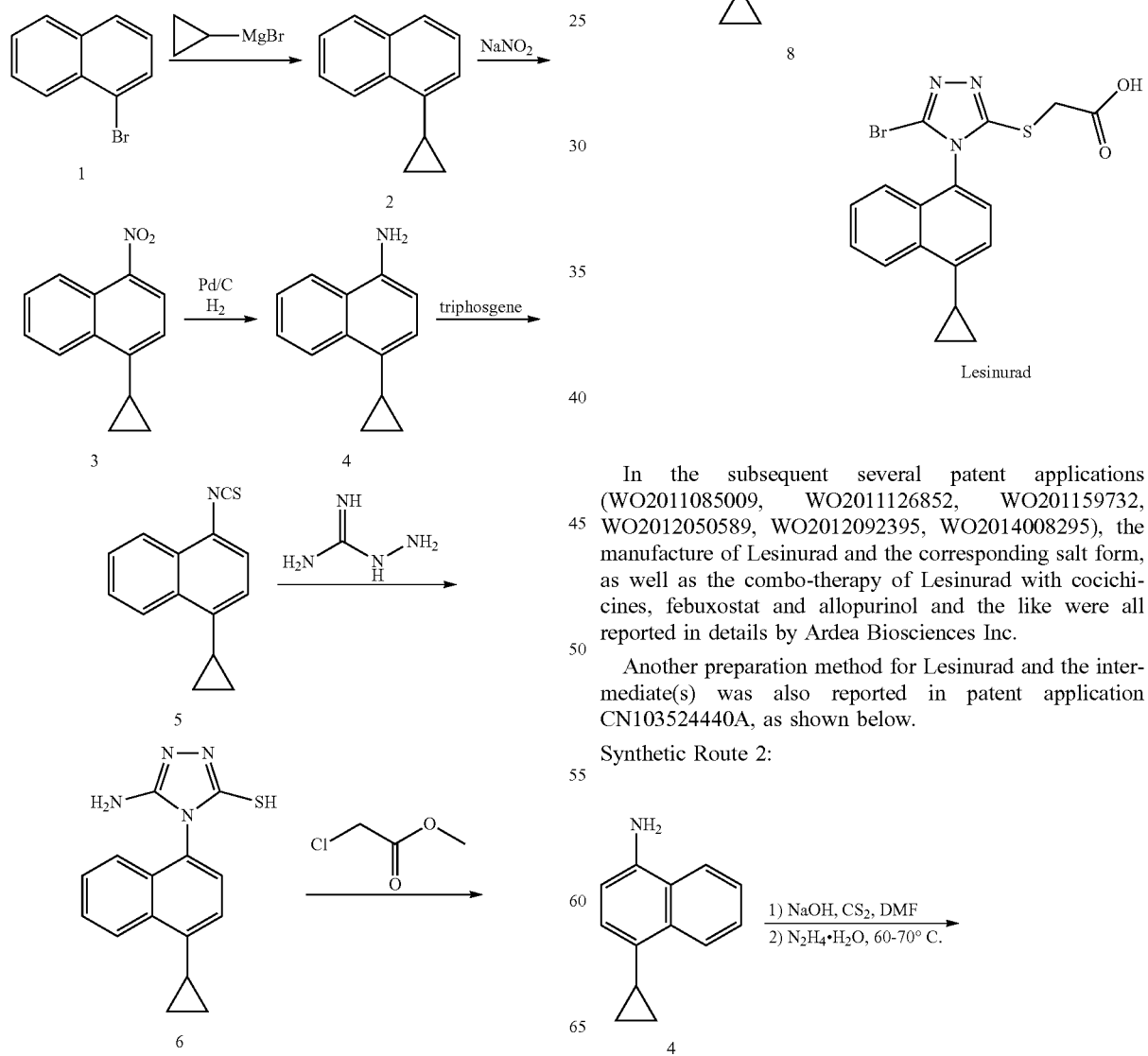

In the subsequent several patent applications (WO2011085009, WO2011126852, WO201159732, WO2012050589, WO2012092395, WO2014008295), the manufacture of Lesinurad and the corresponding salt form, as well as the combo-therapy of Lesinurad with cocichicines, febuxostat and allopurinol and the like were all reported in details by Ardea Biosciences Inc.

Another preparation method for Lesinurad and the intermediate(s) was also reported in patent application CN103524440A, as shown below.

Synthetic Route 2:

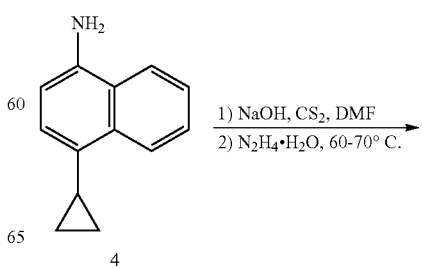

3

-continued

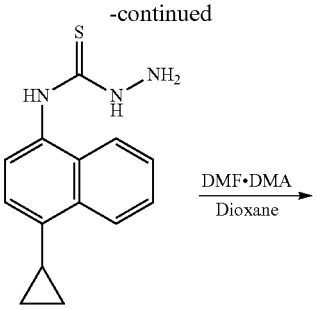

9

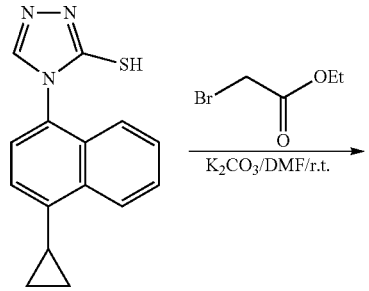

10

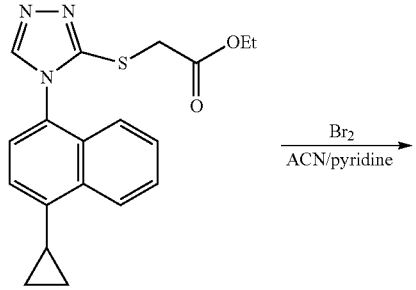

11

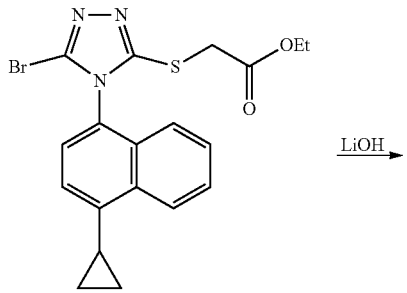

12

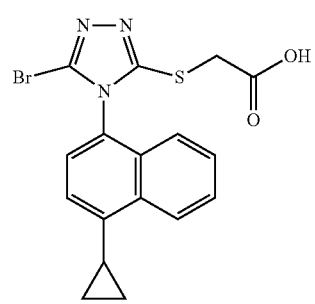

Lesinurad

In these published patent applications, no clear description about Lesinurad as a mixture of axially chiral atropisomers was available, neither details of separation technol-

4 ogy, asymmetric synthesis technology and specific characterization data of these two atropisomers were reported ever.

CONTENTS OF THE PRESENT INVENTION

The present invention provides a laevorotary (L-) or dextrogyrate (D-) compound of formula (I), or a pharmaceutically acceptable salt thereof, in the form of a single axially chiral isomer or enriched in an axially chiral isomer.

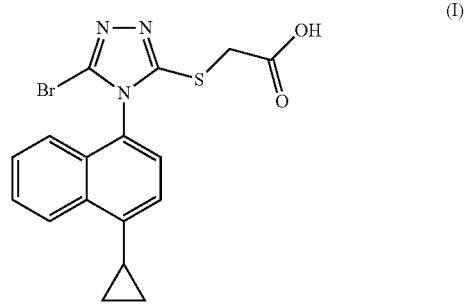 [SMILES: O=C(O)CSc1nnc(Br)n1-c1ccc(C2CC2)c2ccccc12]

(I)

In an embodiment of the present invention, the content of one of the axially chiral isomers is ≥60%, preferably ≥70%, more preferably ≥80%, even more preferably ≥90%, most preferably ≥95%. The present invention also provides a compound of formula (II):

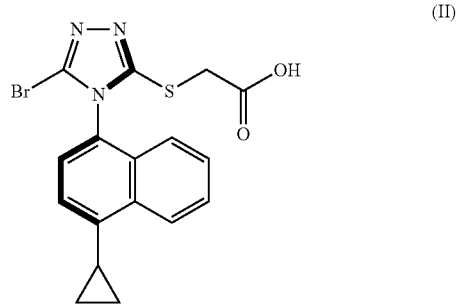

(II)

In an embodiment of the present invention, the excess of the axially chiral isomer of formula (II) is ≥95%. The present invention also provides a compound of formula (III):

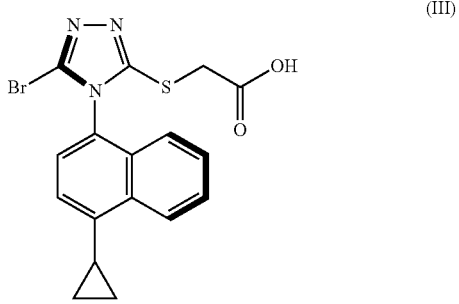

(III)

In an embodiment of the present invention, the excess of the axially chiral isomer of formula (III) is ≥95%.

The present invention also provides a process for the preparation of the compound described above, which comprises the synthetic route of formula (IV):

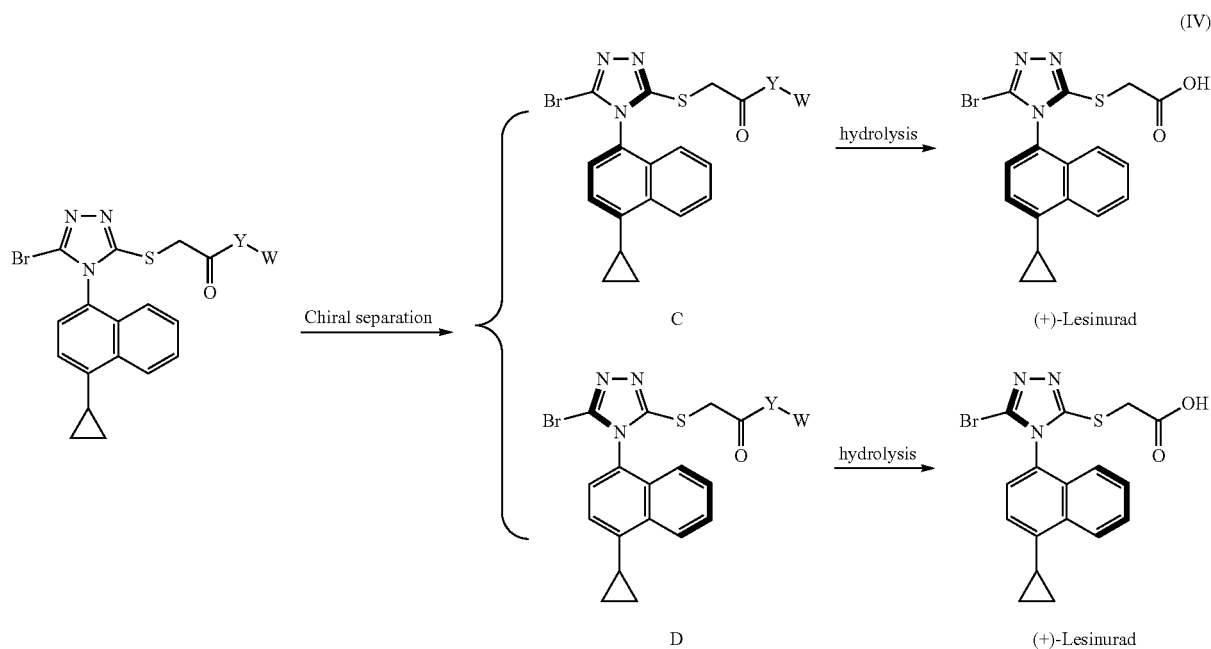

wherein,

Y is selected from O, NH or N (W); W is selected from an alkyl, which is optionally substituted by 1 or 2 or 3 of halogen, OH, CN or $NH_2$;

preferably, the chiral separation refers to the SFC separation;

preferably, W is selected from a $C_{1-6}$ alkyl, which is optionally substituted by 1 or 2 or 3 of halogen, OH, CN or $NH_2$;

preferably, W is selected from methyl, ethyl, propyl, trifluoromethyl, or trifluoroethyl.

The present invention also provides a process for the preparation of the compound described above, which comprises the synthetic route of formula (V):

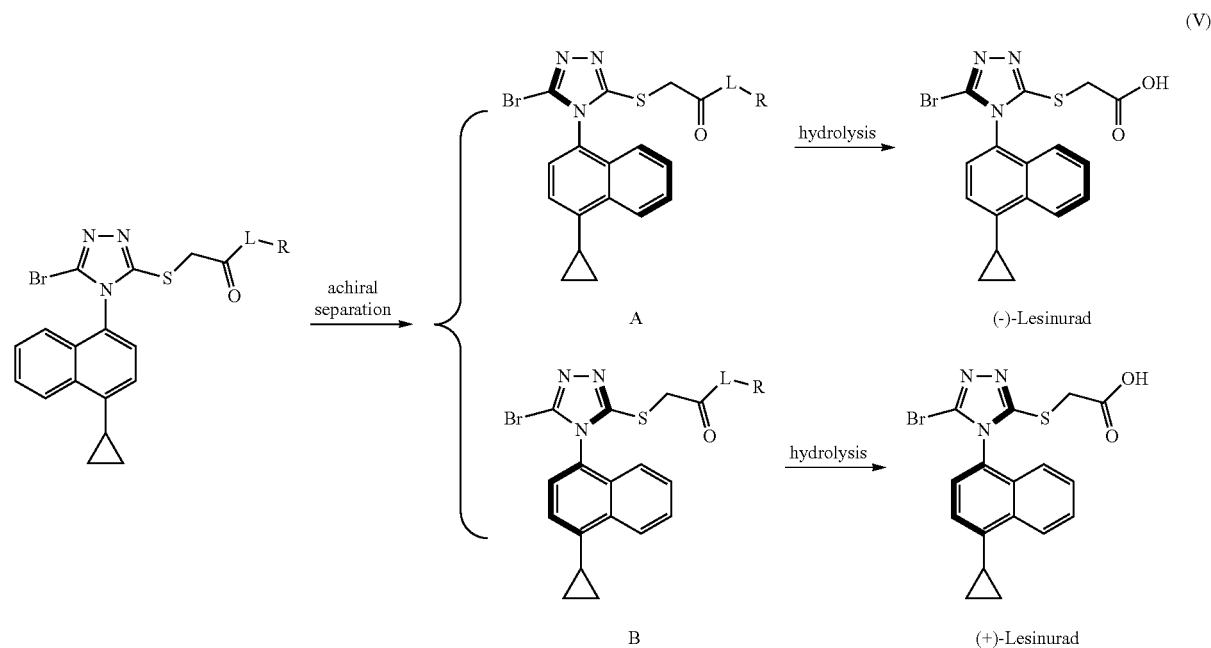

wherein, L is selected from O, NH or N (R);

R represents a chiral group selected from the group consisting of a chiral alkyl, a chiral heteroalkyl, a chiral aralkyl, a chiral heteroaralkyl, and achiral aryl; in which the chiral group is optionally substituted by 1 or 2 or 3 of halogen, OH, CN or $NH_2$;

preferably, the achiral separation refers to recrystallization, thin-layer chromatography separation, column chromatography separation, rapid column separation, and separation using preparative chromatographic columns of achiral fillers.

The present invention also provides a process for the preparation of the compound described above, which comprises the synthetic route of formula (VI):

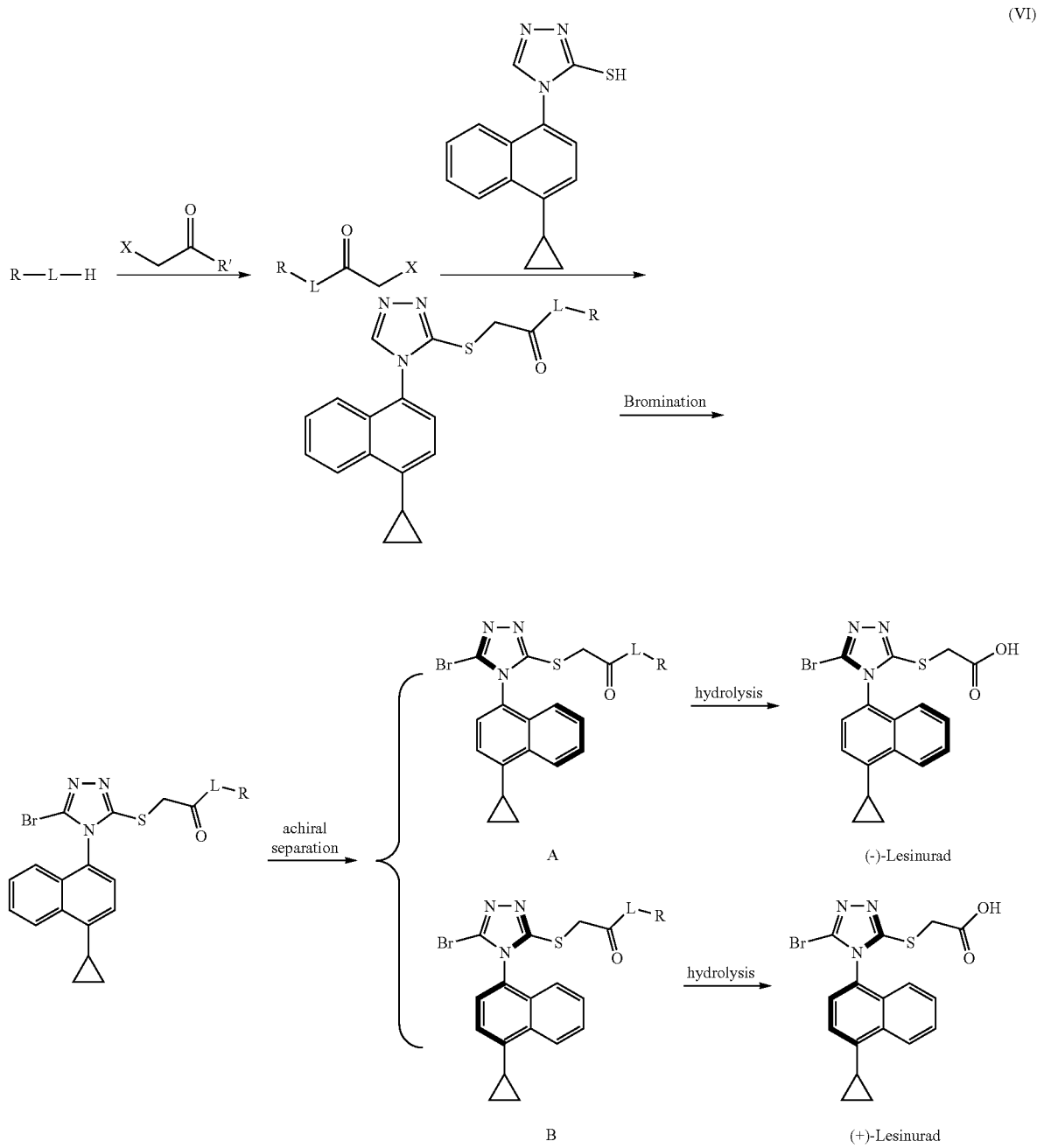

wherein, X is selected from the group consisting of F, Cl, Br, I, and sulfonate; R' is selected from the group consisting of F, Cl, Br, I and OH.

In an embodiment for preparation method of the present invention, the hydrolysis is carried out under strong base conditions.

In an embodiment for preparation method of the present invention, the strong base is preferably selected from LiOH, NaOH, or KOH.

In an embodiment for preparation method of the present invention, the R is selected from phenylalkyl or

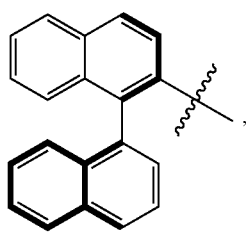

the C on the alkyl group of the phenylalkyl is optionally substituted by one or more of N, O, S, C(=O), C(=O)O, S(=O), S(=O)$_2$, C(=O)NH, S(=O)NH, S(=O)$_2$NH or NHBoc.

In an embodiment for preparation method of the present invention, the R is preferably selected from

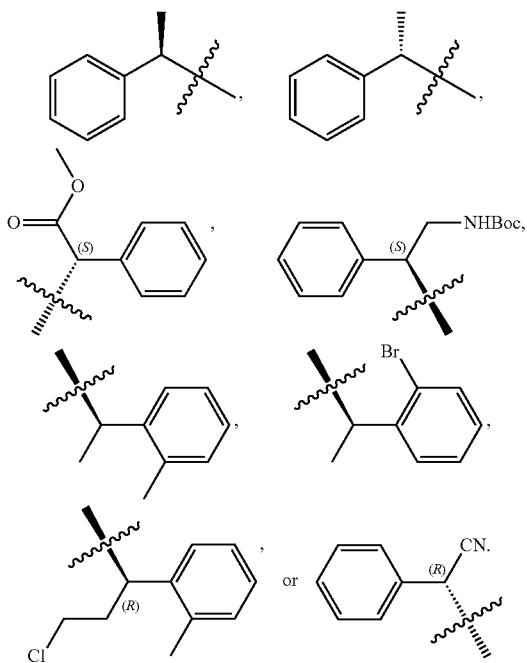

In an embodiment for preparation method of the present invention, the brominating reagent is Br$_2$/base.

In an embodiment for preparation method of the present invention, the base in the brominating reagent is preferably from pyridine, triethylamine, or DIPEA.

In an embodiment for preparation method of the present invention, the sulfonate is selected from methanesulfonate, p-toluenesulfonate, p-nitrobenzenesulfonate or trifluoromethanesulfonate.

The present invention also provides a pharmaceutical composition comprising a therapeutically effective amount of the aforesaid compound or the pharmaceutically acceptable salt thereof as an active ingredient and a pharmaceutically acceptable carrier.

The present invention also provides a use of the aforesaid compound or the pharmaceutically acceptable salt thereof or the aforesaid composition in the manufacture of a medicament for the treatment of disorders associated with abnormal serum uric acid levels.

The present invention also provides a method of treating a condition associated with abnormal serum uric acid level comprising administering to a subject a therapeutically effective amount of the aforesaid compound or the pharmaceutically acceptable salt thereof or the aforesaid composition.

The present invention also provides a use of the aforesaid compound or the pharmaceutically acceptable salt thereof or the aforesaid composition as a medicament for treating a condition associated with abnormal serum uric acid level.

Definitions

In the present invention, unless otherwise specified, the "Lesinurad" refers specifically to the compound of formula (I):

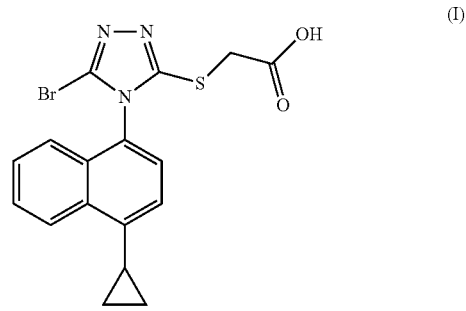 [SMILES: O=C(O)CSc1nnc(Br)n1-c1ccc(C2CC2)c2ccccc12]

The "laevorotary (L-) or dextrogyrate (D-) compound of the formula (I)" may be a single axially chiral isomer of the compound of formula (I), or it may be a mixture enriched in one axially chiral isomer.

"enriched in one axially chiral isomer" refers to the content of one of the axially chiral isomers is <100%, and ≥60%, preferably ≥70%, more preferably ≥80%, even more preferably ≥90%, most preferably ≥95%.

The excess of the axially chiral isomers refers to the difference between the relative percentages of the two axially chiral isomers. For example, the content of one of the axially chiral isomers is 90% and the other one is 10%, then the excess of the axially chiral isomer is 80%.

The compounds of formulas (II) and (III) are two absolute configurations of the compound of formula (I) respectively,

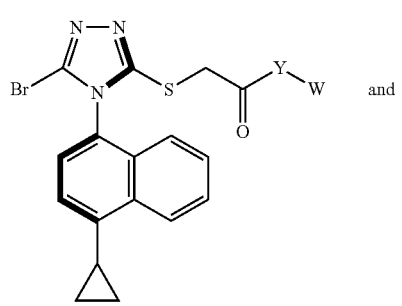 and

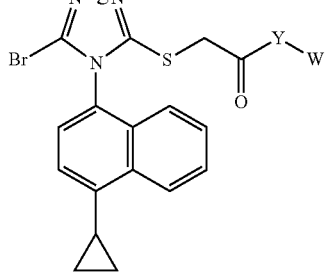
are two absolute configurations of
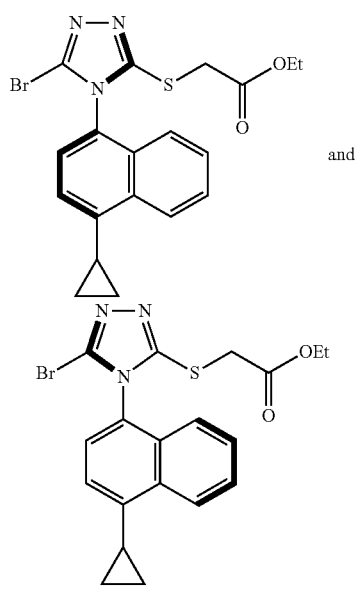
respectively,
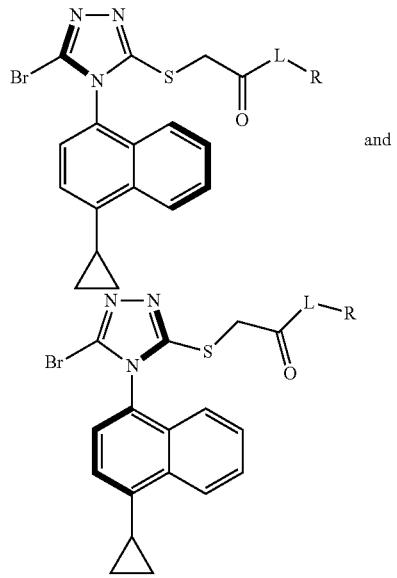
and
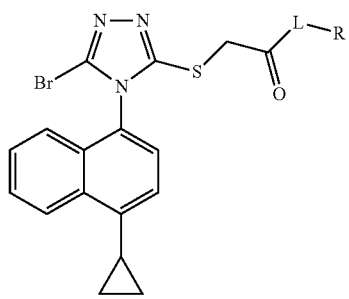
are two absolute configurations of
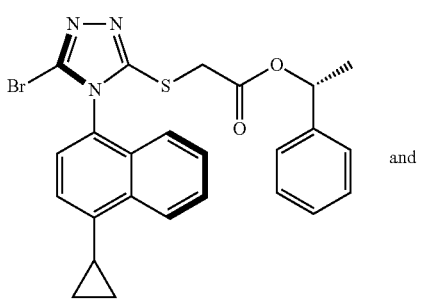
respectively,
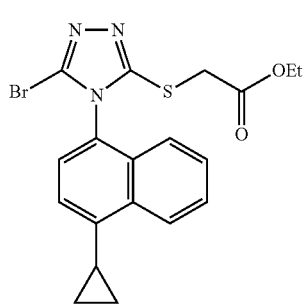 [SMILES: CCOC(=O)CSc1nnc(Br)n1-c1ccc(C2CC2)c2ccccc12]
are two absolute configurations of
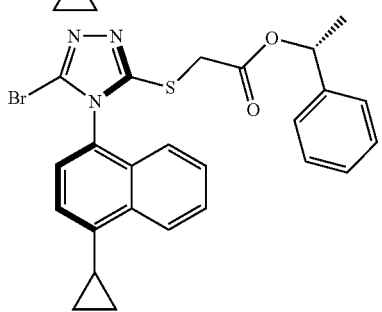
and are two absolute configurations of
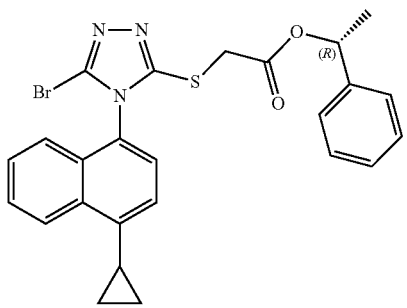
respectively, the structure can be confirmed by single crystal X-ray diffraction.
However, for ease of expression, the content described in
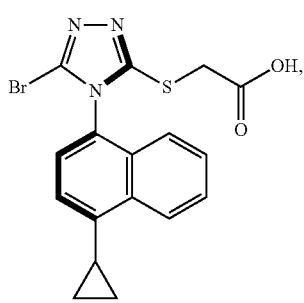
(+)-Lesinurad
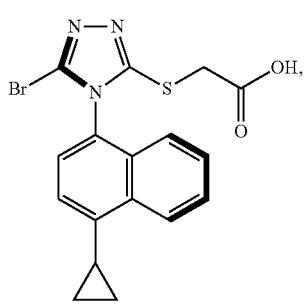
(−)-Lesinurad
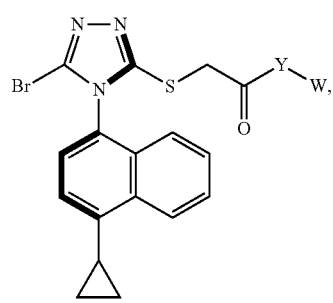
C
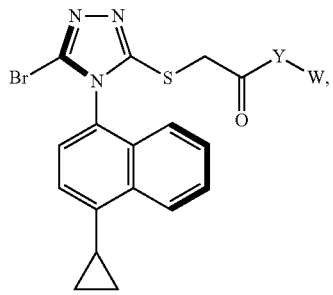
D
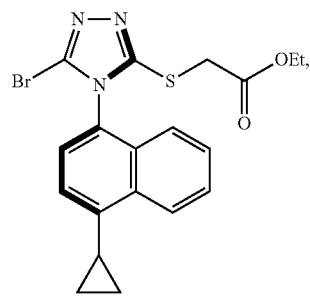
12B
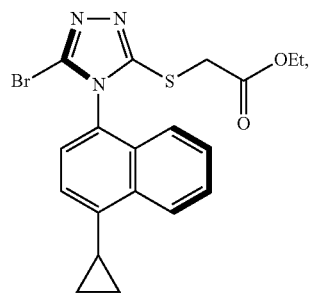
12A
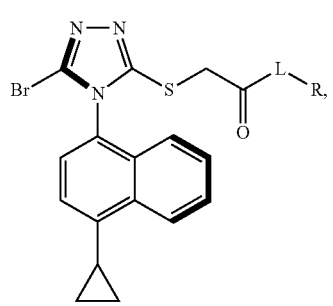
A
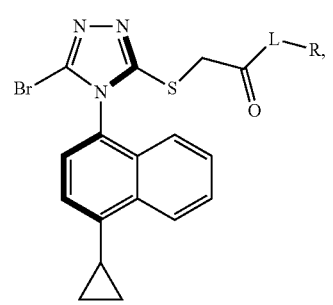
B

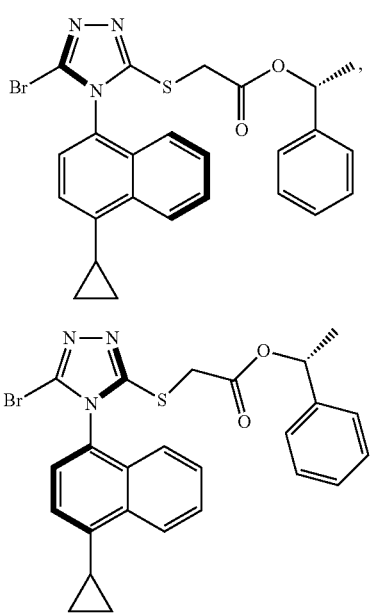

in the synthetic routes and embodiments is not limited to a single axially chiral isomer as defined by the formula, but also includes a mixture enriched in one axially chiral isomer.

(+) represents the dextrorotation, (−) represents the levorotation, and (±) represents the racemization.

The term "aryl" means, unless otherwise stated, a polyunsaturated aromatic substituent that may be mono-, di- or multi-substituted, and can be monovalent, divalent, or polyvalent, or a single ring or multiple rings (such as 1 to 3 of rings; at least one ring is aromatic), which are fused together or linked covalently. The term "heteroaryl" refers to aryl groups (or rings) that contain one to four of heteroatoms. In an exemplary embodiment, the heteroatom is selected from the group consisting of B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "aralkyl" is meant to include those radicals in which an aryl group is attached to an alkyl group (e.g., benzyl, phenethyl, pyridylmethyl and the like), including those alkyl groups in which a carbon atom (e.g., a methylene group) has been replaced by, for example, an oxygen atom, e.g., phenoxymethyl, 2-pyridyloxymethyl, 3-(1-naphthyloxy)propyl, and the like.

DIPEA represents diisopropyl ethylamine; OTos represents p-toluenesulfonate; OMs represents mesylate.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" is meant to include a salt of a compound of the present invention which is prepared by a relatively nontoxic acid or base with the compound of the present invention having particular substituents. When the compound of the present invention contains a relatively acidic functional group, a base addition salt can be obtained by contacting a neutral form of such compounds with a sufficient amount of a desired base, either neat or in a suitable inert solvent. Examples of the pharmaceutically acceptable base addition salts include salts of sodium, potassium, calcium, ammonium, organic amine, or magnesium, or similar salts. When the compound of the present invention contains a relatively basic functional group, an acid addition salt can be obtained by contacting a neutral form of such compounds with a sufficient amount of a desired acid, either neat or in a suitable inert solvent. Examples of the pharmaceutically acceptable acid addition salts include salts of inorganic acids including hydrochloric, hydrobromic, nitric, carbonic, hydrocarbonic, phosphoric, hydrophosphoric, dihydrophosphoric, sulfuric, hydrosulfuric, hydriodic, or phosphorous acids and the like; as well as salts of organic acids including acetic, propionic, isobutyric, maleic, malonic, benzoic, succinic, suberic, fumaric, lactic, mandelic, phthalic, benzenesulfonic, p-tolylsulfonic, citric, tartaric, methanesulfonic acid, or the like; and also salts of amino acids (such as arginate and the like), and salts of organic acids like glucuronic acid and the like (see, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral form of the compound is preferably regenerated by contacting the salt with a base or acid and then isolating the parent compounds in the conventional manner. The parent form of the compound differs from the various salt forms thereof in certain physical properties, such as solubility in polar solvents.

As used herein, the term "pharmaceutically acceptable salts" refers to derivatives of the compound of the present invention wherein the parent compound is modified by making a salt with an acid or base. Examples of pharmaceutically acceptable salts include, but are not limited to, inorganic or organic acid salts of basic groups such as amines; alkali or organic salts of acidic groups such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodide, hydroxyl acids, hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and p-toluene sulfonic acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile or the like are preferred.

The compounds of the present invention may also contain unnatural proportions of atomic isotopes at one or more of the atoms that constitute such compounds. For example, the compounds may be radiolabeled with radioactive isotopes, such as tritium ($^3$H), iodine-125 ($^{125}$I) or carbon-14 ($^{14}$C). All isotopic variations of the compounds of the present invention, regardless of radioactivity or not, are intended to be encompassed within the scope of the present invention.

The term "pharmaceutically acceptable carrier" refers to any formulation or carrier medium that is capable of delivery of an effective amount of an active agent of the present invention, and does not interfere with the biological activity of the active agent, without toxic side effects in a host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005), which is incorporated herein by reference.

The terms "effective amount" or "therapeutically effective amount" for a drug or pharmacologically active agent refers to a nontoxic but sufficient amount of the drug or agent to provide the desired effect. In the oral dosage forms of the present disclosure, an "effective amount" of an active agent of the composition refers to the amount of the active agent required to provide the desired effect when used in combination with the other active agent of the composition. The amount that is "effective" will vary from subject to subject, depending on the age and general condition of a recipient, and also a particular active agent, and an appropriate effective amount in an individual case may be determined by one of ordinary skill in the art using routine experimentation.

The terms "active ingredient," "therapeutic agent," "active substance," or "active agent" mean a chemical entity which can be effective in treating a targeted disorder, disease or condition.

The term "optional" or "optionally" means that the subsequently described event or circumstance may but need not occur, and that the description includes instances where the event or circumstance occurs and instances in which it does not. For example, the ethyl group is "optionally" substituted by a halogen, meaning that the ethyl group may be unsubstituted ($CH_2CH_3$), monosubstituted (e.g., $CH_2CH_2F$), poly (e.g., $CHFCH_2F, CH_2CHF_2$, etc.) or fully substituted ($CF_2CF_3$).

The term "substituted", means that any one or more hydrogens on a designated atom is replaced with a substituent, provided that the designated atom's valency is normal, and that the substituted compound is stable. When a substituent is keto (i.e., =O), it means that 2 hydrogen atoms are replaced. Keto substituents are not present on aromatic moieties. The term "optionally substituted" means that the designated atom can be substituted or unsubstituted, and unless otherwise stated, the species and number of the substituents may be arbitrary provided that they can be achieved in chemistry.

When any variable (e.g., R) occurs more than once in the constituent or structure of a compound, its definition at each occurrence is independent. Thus, for example, if a group is substituted with 0-2 of R(s), then said group may optionally be substituted with up to two R groups and R at each occurrence has independently options. Also, combinations of substituents and/or variables are permissible only if such combinations result in stable compounds.

The Advantage of the Present Invention

The atropisomerism of Lesinurad due to the axis chirality was identified. (+)-Lesinurad and (−)-Lesinruad were further proved to be stable in ambient temperature and in plasmas. Thus it is reasonable to develop the single atropisomer of Lesinurad for clinical use.

The stability data of (+)-Lesinurad and (−)-Lesinruad in solid form, in normal organic solvents and in plamsas was reported in details. On the stable-transfected URAT1-HEK293 cell line, the inhibition potency of (+)-Lesinurad and (−)-Lesinruad for the URAT1 mediated uptake of labeling uric acid was also reported in details, together with the pharmacokinetic parameters in rats. Based on these data, we could conclude that the solid (+)-Lesinurad and (−)-Lesinurad were stable enough in ambient temperature or in solvent. (+)-Lesinurad showed obvious higher in vitro inhibition potency again URAT1 compared with (−)-Lesinurad and racemic (±)-Lesinurad. In the pharmacokinetic studies in rats, the transformation of (+)-Lesinurad and (−)-Lesinurad was not observed. These two atropisomers were stable isomers in vivo.

In the synthetic methods reported in the present patent, the synthetic route formulas (V) and (VI) involve no chiral separation so that huge cost is saved.

DETAILED DESCRIPTION OF THE INVENTION

The following examples and tests further demonstrate the present invention and are not meant to be limiting of the scope of the present invention. While the present invention has been described in detail and with reference to specific embodiments thereof, it will be apparent to one skilled in the art that various changes and modifications can be made therein without departing from the spirit and scope thereof.

Example 1: Preparation of (−)-Lesinurad and (+)-Lesinurad

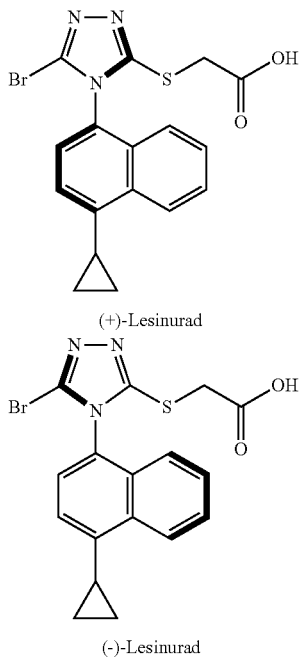

(+)-Lesinurad (−)-Lesinurad

Synthetic Route:

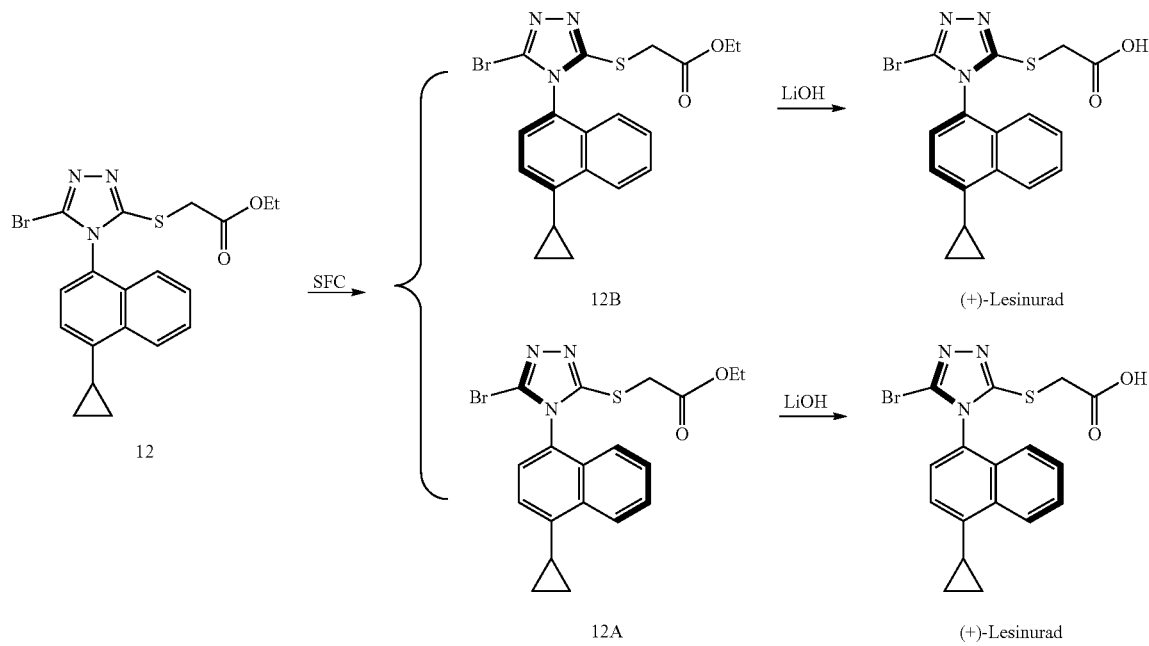

Step 1: Preparation of 12A and 12B

Compound 12 was prepared according to the method reported by patent application W2009/070740 or CN103524440A. Compound 12 (330.00 mg, 763.31 μmop) was separated by supercritical fluid chromatography SFC (chiral column: Chiralpak AS (250 mm×30 mm, 5 um); eluent: supercritical $CO_2$/ethanol (0.05% DEA)=70/30; flow rate: 60 mL/min; detection wavelength: 220 nm) to give 12A (150.00 mg, 346.96 μmop and 12B (152.00 mg, 351.58 μmop.

Figure 1:
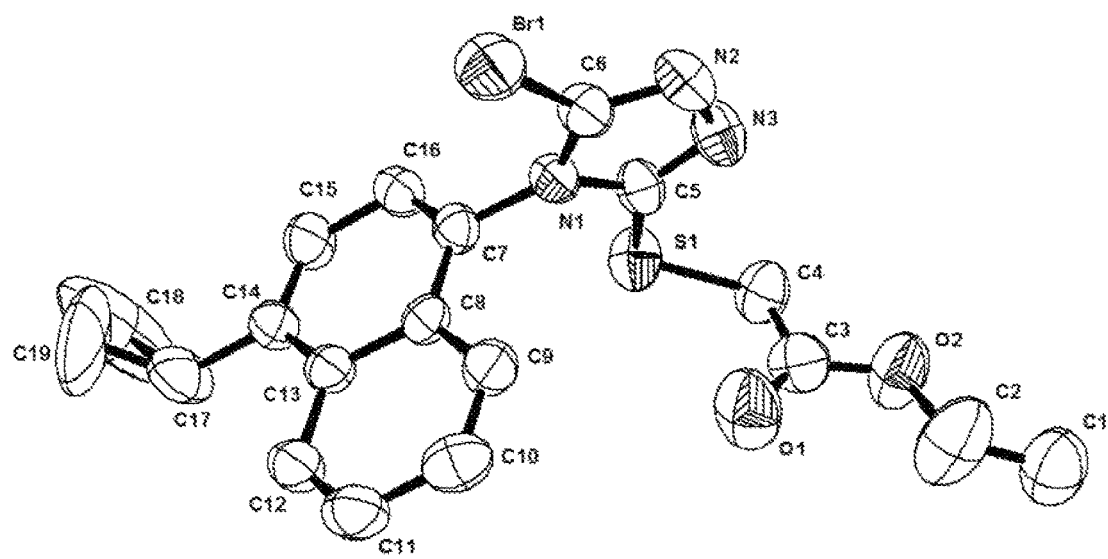
FIG. 1: The stereospecific ellipsoid of compound 12A single molecule.
Figure 2:
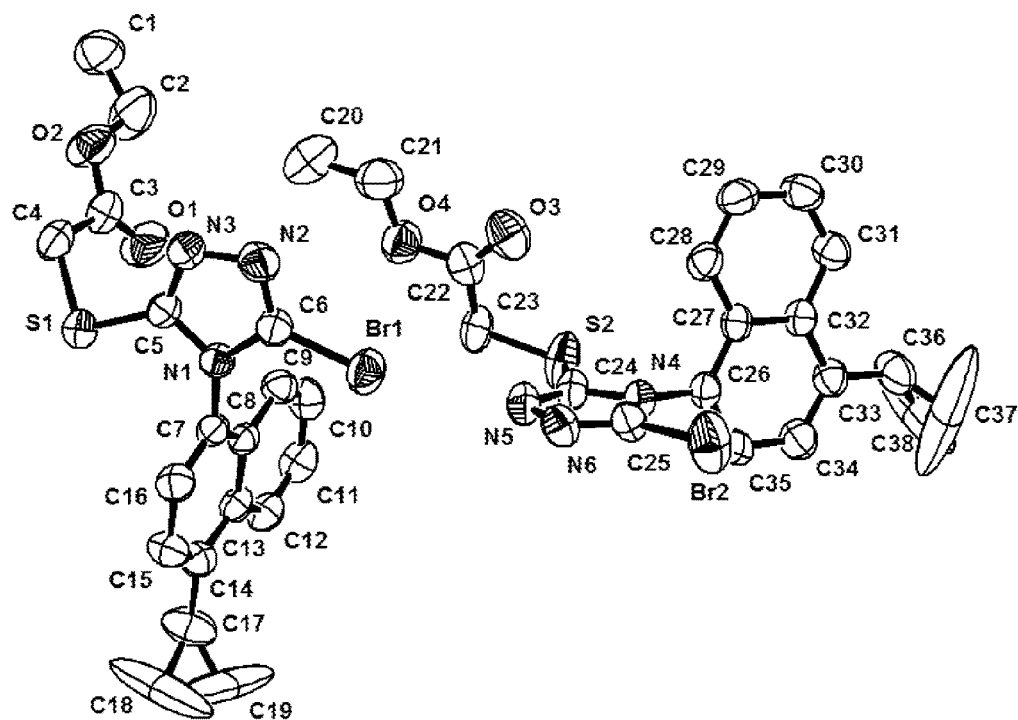
FIG. 2: The stereospecific ellipsoid of compound 12A bimolecular.
Figure 3:
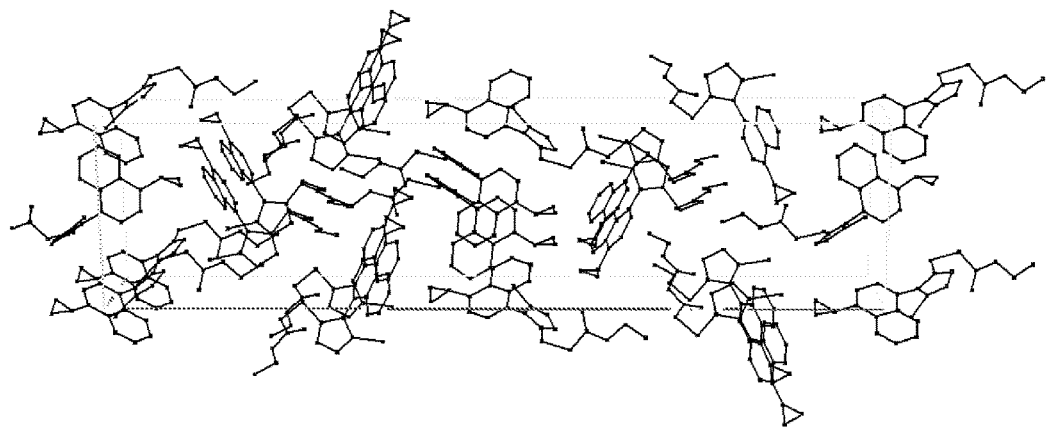
FIG. 3: The unit cell stacking diagram of compound 12A in the direction of a axis.

Compound 12A: $^1$H-NMR (400 MHz, DMSO-$d_6$, δ): 8.57 (d, J=8.4 Hz, 1H), 7.78-7.76 (m, 1H), 7.69-7.58 (m, 2H), 7.43 (d, J=7.6 Hz, 1H), 7.13 (d, J=8.0 Hz, 1H), 4.10-4.00 (m, 4H), 2.59-2.51 (m, 1H), 1.17-1.11 (m, 5H), 0.89-0.83 (m, 2H). SFC (chiral column: Chiralpak AS-H (250 mm×4.6 mm, 5 um); eluent: ethanol (0.05% DEA)/supercritical $CO_2$=5-40%; flow rate: 2.5 mL/min; detection wavelength: 220 nm): $R_t$=4.842 min., e.e.=100%. $[\alpha]^{25}_D$=−11.036 (c=9.455 mg/mL in ethanol). The single crystal X-ray structure information of compound 12A was shown in FIG. 1-3 with detailed data below.

The Single Crystal X-Ray Structure Refinement Information of Compound 12A

| | |
|---|---|
| Identification code | 12A |
| Empirical formula | C19H18BrN3O2S |
| Formula weight | 432.33 |
| Temperature | 296(2) K |
| Wavelength | 1.54178 A |
| Crystal system, space group | Orthorhombic, P 21 21 21 |
| Unit cell dimensions | a = 7.29790(10) A    alpha = 90 deg. |
| | b = 11.3584(2) A    beta = 90 deg. |
| | c = 46.6559(7) A    gamma = 90 deg. |
| Volume | 3867.42(10) A^3 |
| Z, Calculated density | 8, 1.485 Mg/m^3 |
| Absorption coefficient | 4.058 mm −1 |
| F(000) | 1760 |

-continued

| | |
|---|---|
| Crystal size | 0.10 × 0.12 × 0.40 mm |
| Theta range for data collection | 3.790 to 67.485 deg. |
| Limiting indices | −7 <= h <= 8, −12 <= k <= 13, |
| | −49 <= l <= 55 |

-continued

| Reflections collected/unique | 18079/6618 [R(int) = 0.0277] |
| --- | --- |
| Completeness to theta = 67.485 | 96.2% |
| Refinement method | Full-matrix least-squares on $F^2$ |
| Data/restraints/parameters | 6618/0/469 |
| Goodness-of-fit on $F^2$ | 1.024 |
| Final R indices [I > 2sigma(I)] | R1 = 0.0377, wR2 = 0.1018 |
| R indices (all data) | R1 = 0.0389, wR2 = 0.1030 |
| Absolute structure parameter | 0.019(6) |
| Extinction coefficient | n/a |
| Largest diff. peak and hole | 0.516 and −0.458 e · $Å^{-3}$ |

Atomic Coordinate Parameters and Equivalent Temperature Factor Values of Compound 12A

| | x | y | z | U(eq) |
| --- | --- | --- | --- | --- |
| C(37) | 1920(20) | 10880(30) | 4191(3) | 380(20) |
| C(18) | 7640(20) | 421(11) | 6367(5) | 240(13) |
| C(19) | 7080(30) | 849(12) | 6145(4) | 248(12) |
| Br(1) | 6241(1) | 7039(1) | 6427(1) | 68(1) |
| S(1) | 5006(2) | 4584(1) | 7431(1) | 62(1) |
| N(1) | 5659(5) | 5619(3) | 6918(1) | 44(1) |
| N(2) | 5657(7) | 7516(3) | 7011(1) | 58(1) |
| C(13) | 4337(6) | 3021(4) | 6467(1) | 44(1) |
| C(4) | 3535(8) | 5278(5) | 7690(1) | 63(1) |
| N(3) | 5297(7) | 6904(4) | 7265(1) | 60(1) |
| C(8) | 4237(6) | 4146(4) | 6603(1) | 40(1) |
| C(7) | 5743(6) | 4509(4) | 6770(1) | 42(1) |
| C(5) | 5316(7) | 5787(4) | 7203(1) | 47(1) |
| C(14) | 5919(7) | 2302(4) | 6509(1) | 49(1) |
| C(9) | 2638(7) | 4832(4) | 6565(1) | 50(1) |
| C(3) | 1694(8) | 5621(5) | 7569(1) | 63(1) |
| O(2) | 835(6) | 6298(5) | 7754(1) | 87(1) |
| O(1) | 1071(7) | 5324(5) | 7345(1) | 95(2) |
| C(15) | 7317(7) | 2703(4) | 6675(1) | 56(1) |
| C(2) | −980(11) | 6714(9) | 7670(2) | 108(3) |
| C(11) | 1331(7) | 3346(5) | 6268(1) | 62(1) |
| C(10) | 1232(7) | 4455(5) | 6403(1) | 61(1) |
| C(16) | 7249(7) | 3826(4) | 6808(1) | 50(1) |
| C(17) | 6026(9) | 1109(5) | 6373(2) | 79(2) |
| C(12) | 2816(7) | 2652(4) | 6300(1) | 54(1) |
| C(1) | −1961(11) | 7100(8) | 7916(2) | 94(2) |
| Br(2) | 8340(1) | 9744(1) | 5253(1) | 86(1) |
| S(2) | 1869(2) | 7862(2) | 5638(1) | 76(1) |
| O(4) | 1453(6) | 8018(3) | 6479(1) | 69(1) |
| C(26) | 3950(6) | 9335(4) | 5175(1) | 44(1) |
| N(5) | 5502(6) | 7811(4) | 5805(1) | 56(1) |
| C(28) | 2994(7) | 11029(4) | 5473(1) | 51(1) |
| C(31) | 1300(7) | 12038(4) | 5000(1) | 54(1) |
| N(4) | 4909(5) | 8829(3) | 5414(1) | 45(1) |
| O(3) | 2342(6) | 9397(4) | 6164(1) | 81(1) |
| N(6) | 7142(5) | 8292(4) | 5705(1) | 55(1) |
| C(27) | 3052(6) | 10436(4) | 5209(1) | 41(1) |
| C(34) | 3074(9) | 9265(5) | 4682(1) | 65(1) |
| C(6) | 5850(7) | 6733(4) | 6815(1) | 49(1) |
| C(30) | 1289(8) | 12603(4) | 5254(1) | 63(1) |
| C(25) | 6725(7) | 8874(4) | 5477(1) | 49(1) |
| C(22) | 1858(7) | 8413(5) | 6217(1) | 58(1) |
| C(32) | 2177(6) | 10930(4) | 4964(1) | 43(1) |
| C(33) | 2211(7) | 10320(4) | 4697(1) | 53(1) |
| C(29) | 2119(8) | 12085(5) | 5493(1) | 61(1) |
| C(35) | 3958(9) | 8762(4) | 4920(1) | 58(1) |
| C(24) | 4214(7) | 8139(4) | 5628(1) | 50(1) |
| C(23) | 1596(8) | 7437(5) | 6005(1) | 62(1) |
| C(36) | 1284(12) | 10829(8) | 4440(1) | 84(2) |
| C(21) | 1711(11) | 8828(6) | 6715(1) | 81(2) |
| C(20) | 906(12) | 8259(8) | 6974(2) | 100(2) |
| C(38) | 610(30) | 10309(8) | 4213(3) | 282(15) |

Bond Length and Bond Angular Values of Bonded Atoms of Compound 12A

| C(37)—C(38) | 1.16(3) |
| --- | --- |
| C(37)—C(36) | 1.250(15) |
| C(18)—C(19) | 1.21(3) |
| C(18)—C(17) | 1.413(12) |
| C(19)—C(17) | 1.346(12) |
| Br(1)—C(6) | 1.866(5) |
| S(1)—C(5) | 1.747(5) |
| S(1)—C(4) | 1.798(5) |
| N(1)—C(6) | 1.362(6) |
| N(1)—C(5) | 1.365(6) |
| N(1)—C(7) | 1.439(5) |
| N(2)—C(6) | 1.285(6) |
| N(2)—N(3) | 1.398(6) |
| C(13)—C(12) | 1.421(7) |
| C(13)—C(14) | 1.427(7) |
| C(13)—C(8) | 1.427(6) |
| C(4)—C(3) | 1.509(8) |
| N(3)—C(5) | 1.302(6) |
| C(8)—C(7) | 1.411(6) |
| C(8)—C(9) | 1.413(6) |
| C(7)—C(16) | 1.357(7) |
| C(14)—C(15) | 1.360(7) |
| C(14)—C(17) | 1.498(7) |
| C(9)—C(10) | 1.347(7) |
| C(3)—O(1) | 1.185(7) |
| C(3)—O(2) | 1.316(7) |
| O(2)—C(2) | 1.461(9) |
| C(15)—C(16) | 1.419(7) |
| C(2)—C(1) | 1.425(10) |
| C(11)—C(12) | 1.349(8) |
| C(11)—C(10) | 1.410(8) |
| Br(2)—C(25) | 1.859(5) |
| S(2)—C(24) | 1.741(5) |
| S(2)—C(23) | 1.788(5) |
| O(4)—C(22) | 1.332(6) |
| O(4)—C(21) | 1.448(7) |
| C(26)—C(35) | 1.356(6) |
| C(26)—C(27) | 1.421(6) |
| C(26)—N(4) | 1.434(5) |
| N(5)—C(24) | 1.305(6) |
| N(5)—N(6) | 1.397(6) |
| C(28)—C(29) | 1.362(7) |
| C(28)—C(27) | 1.404(6) |
| C(31)—C(30) | 1.351(7) |
| C(31)—C(32) | 1.422(7) |
| N(4)—C(25) | 1.359(6) |
| N(4)—C(24) | 1.370(6) |
| O(3)—C(22) | 1.198(6) |
| N(6)—C(25) | 1.286(6) |
| C(27)—C(32) | 1.427(6) |
| C(34)—C(33) | 1.356(8) |
| C(34)—C(35) | 1.407(7) |
| C(30)—C(29) | 1.398(8) |
| C(22)—C(23) | 1.500(8) |
| C(32)—C(33) | 1.423(6) |
| C(33)—C(36) | 1.493(7) |
| C(36)—C(38) | 1.313(10) |
| C(21)—C(20) | 1.494(10) |
| C(38)—C(37)—C(36) | 65.9(10) |
| C(19)—C(18)—C(17) | 61.2(7) |
| C(18)—C(19)—C(17) | 66.9(11) |
| C(5)—S(1)—C(4) | 98.3(2) |
| C(6)—N(1)—C(5) | 103.6(4) |
| C(6)—N(1)—C(7) | 129.7(4) |
| C(5)—N(1)—C(7) | 126.7(4) |
| C(6)—N(2)—N(3) | 106.3(4) |
| C(12)—C(13)—C(14) | 122.6(4) |
| C(12)—C(13)—C(8) | 117.9(4) |
| C(14)—C(13)—C(8) | 119.6(4) |
| C(3)—C(4)—S(1) | 113.1(4) |
| C(5)—N(3)—N(2) | 107.2(4) |
| C(7)—C(8)—C(9) | 123.4(4) |
| C(7)—C(8)—C(13) | 117.8(4) |
| C(9)—C(8)—C(13) | 118.8(4) |
| C(16)—C(7)—C(8) | 122.4(4) |
| C(16)—C(7)—N(1) | 118.3(4) |

-continued

| | |
|---|---|
| C(8)—C(7)—N(1) | 119.3(4) |
| N(3)—C(5)—N(1) | 110.7(4) |
| N(3)—C(5)—S(1) | 128.8(4) |
| N(1)—C(5)—S(1) | 120.5(3) |
| C(15)—C(14)—C(13) | 119.6(4) |
| C(15)—C(14)—C(17) | 120.3(5) |
| C(13)—C(14)—C(17) | 120.1(5) |
| C(10)—C(9)—C(8) | 121.5(5) |
| O(1)—C(3)—O(2) | 124.2(6) |
| O(1)—C(3)—C(4) | 126.7(6) |
| O(2)—C(3)—C(4) | 109.1(4) |
| C(3)—O(2)—C(2) | 116.2(5) |
| C(14)—C(15)—C(16) | 121.5(5) |
| C(1)—C(2)—O(2) | 109.6(6) |
| C(12)—C(11)—C(10) | 120.9(5) |
| C(9)—C(10)—C(11) | 119.8(5) |
| C(7)—C(16)—C(15) | 119.1(4) |
| C(19)—C(17)—C(18) | 52.0(11) |
| C(19)—C(17)—C(14) | 124.2(8) |
| C(18)—C(17)—C(14) | 123.6(7) |
| C(11)—C(12)—C(13) | 121.1(5) |
| C(24)—S(2)—C(23) | 100.5(3) |
| C(22)—O(4)—C(21) | 117.0(5) |
| C(35)—C(26)—C(27) | 121.5(4) |
| C(35)—C(26)—N(4) | 119.1(4) |
| C(27)—C(26)—N(4) | 119.4(4) |
| C(24)—N(5)—N(6) | 107.0(4) |
| C(29)—C(28)—C(27) | 119.8(4) |
| C(30)—C(31)—C(32) | 121.8(4) |
| C(25)—N(4)—C(24) | 102.9(4) |
| C(25)—N(4)—C(26) | 129.1(4) |
| C(24)—N(4)—C(26) | 128.0(4) |
| C(25)—N(6)—N(5) | 106.0(4) |
| C(28)—C(27)—C(26) | 122.3(4) |
| C(28)—C(27)—C(32) | 120.1(4) |
| C(26)—C(27)—C(32) | 117.6(4) |
| C(33)—C(34)—C(35) | 122.0(5) |
| N(2)—C(6)—N(1) | 112.2(4) |
| N(2)—C(6)—Br(1) | 125.4(4) |
| N(1)—C(6)—Br(1) | 122.3(3) |
| C(31)—C(30)—C(29) | 119.9(5) |
| N(6)—C(25)—N(4) | 113.1(4) |
| N(6)—C(25)—Br(2) | 125.9(4) |
| N(4)—C(25)—Br(2) | 121.0(3) |
| O(3)—C(22)—O(4) | 124.7(6) |
| O(3)—C(22)—C(23) | 126.1(5) |
| O(4)—C(22)—C(23) | 109.2(4) |
| C(33)—C(32)—C(31) | 122.8(4) |
| C(33)—C(32)—C(27) | 120.1(4) |
| C(31)—C(32)—C(27) | 117.1(4) |
| C(34)—C(33)—C(32) | 119.0(4) |
| C(34)—C(33)—C(36) | 120.7(5) |
| C(32)—C(33)—C(36) | 120.3(5) |
| C(28)—C(29)—C(30) | 121.3(5) |
| C(26)—C(35)—C(34) | 119.8(4) |
| N(5)—C(24)—N(4) | 111.0(4) |
| N(5)—C(24)—S(2) | 129.8(4) |
| N(4)—C(24)—S(2) | 119.1(4) |
| C(22)—C(23)—S(2) | 114.8(4) |
| C(37)—C(36)—C(38) | 53.7(14) |
| C(37)—C(36)—C(33) | 126.6(10) |
| C(38)—C(36)—C(33) | 130.3(6) |
| O(4)—C(21)—C(20) | 106.9(6) |
| C(37)—C(38)—C(36) | 60.4(11) |

Anisotropic Temperature Factors Values of Compound 12A

| | U11 | U22 | U33 | U23 | U13 | U12 |
|---|---|---|---|---|---|---|
| C(37) | 115(11) | 880(60) | 151(12) | 300(30) | 28(10) | 70(20) |
| C(18) | 176(12) | 102(9) | 440(30) | −143(14) | −178(18) | 92(9) |
| C(19) | 330(20) | 122(10) | 290(20) | −130(13) | 230(20) | −65(12) |
| Br(1) | 87(1) | 64(1) | 54(1) | 9(1) | 10(1) | −14(1) |

-continued

| | U11 | U22 | U33 | U23 | U13 | U12 |
|---|---|---|---|---|---|---|
| S(1) | 80(1) | 57(1) | 48(1) | 8(1) | 7(1) | 10(1) |
| N(1) | 48(2) | 41(2) | 42(2) | −1(1) | −1(2) | −4(1) |
| N(2) | 71(3) | 44(2) | 60(2) | −6(2) | −13(2) | −3(2) |
| C(13) | 47(2) | 47(2) | 37(2) | 0(2) | 4(2) | −10(2) |
| C(4) | 72(3) | 77(3) | 40(2) | 2(2) | 6(2) | 7(3) |
| N(3) | 81(3) | 53(2) | 46(2) | −7(2) | −9(2) | 6(2) |
| C(8) | 42(2) | 45(2) | 34(2) | 2(2) | 6(2) | −1(2) |
| C(7) | 48(2) | 42(2) | 35(2) | −1(2) | 2(2) | −1(2) |
| C(5) | 55(3) | 48(2) | 37(2) | −4(2) | −6(2) | 3(2) |
| C(14) | 53(3) | 41(2) | 52(2) | −3(2) | 4(2) | −6(2) |
| C(9) | 49(3) | 50(2) | 52(2) | 0(2) | 4(2) | 1(2) |
| C(3) | 67(3) | 77(3) | 44(3) | 2(2) | −5(2) | −4(3) |
| O(2) | 69(3) | 132(4) | 60(2) | −25(2) | −11(2) | 28(3) |
| O(1) | 97(3) | 120(4) | 68(3) | −26(3) | −26(2) | 21(3) |
| C(15) | 53(3) | 49(3) | 66(3) | −6(2) | −2(2) | 10(2) |
| C(2) | 79(3) | 178(6) | 68(4) | −5(5) | −12(3) | 39(5) |
| C(11) | 50(3) | 81(3) | 53(3) | −3(2) | −7(2) | −15(2) |
| C(10) | 47(3) | 71(3) | 64(3) | 10(2) | −4(2) | 1(2) |
| C(16) | 51(3) | 51(2) | 49(2) | −7(2) | −5(2) | −4(2) |
| C(17) | 67(4) | 50(3) | 120(5) | −26(3) | −8(4) | −1(2) |
| C(12) | 58(3) | 58(3) | 47(2) | −6(2) | 0(2) | −14(2) |
| C(1) | 81(5) | 111(5) | 88(4) | −15(4) | −6(4) | 23(4) |
| Br(2) | 51(1) | 101(1) | 105(1) | 45(1) | 4(1) | −10(1) |
| S(2) | 60(1) | 112(1) | 56(1) | 29(1) | −11(1) | −31(1) |
| O(4) | 77(3) | 69(2) | 60(2) | 3(2) | 6(2) | −6(2) |
| C(26) | 42(2) | 48(2) | 43(2) | 9(2) | 2(2) | 0(2) |
| N(5) | 65(3) | 55(2) | 46(2) | 11(2) | −6(2) | −2(2) |
| C(28) | 54(3) | 58(3) | 40(2) | 1(2) | −4(2) | 2(2) |
| C(31) | 52(3) | 56(3) | 55(2) | 3(2) | −10(2) | 6(2) |
| N(4) | 48(2) | 44(2) | 43(2) | 9(2) | −1(2) | −1(2) |
| O(3) | 81(3) | 65(2) | 97(3) | 15(2) | 0(2) | −13(2) |
| N(6) | 66(3) | 52(2) | 59(2) | 7(2) | −6(2) | 3(2) |
| C(27) | 40(2) | 43(2) | 40(2) | 5(2) | 0(2) | −7(2) |
| C(34) | 95(4) | 57(3) | 44(3) | −6(2) | −15(3) | 3(3) |
| C(6) | 55(3) | 46(2) | 45(2) | −1(2) | −1(2) | −6(2) |
| C(30) | 62(3) | 55(3) | 71(3) | −4(2) | −3(3) | 16(2) |
| C(25) | 45(3) | 46(2) | 57(3) | 10(2) | 1(2) | 1(2) |
| C(22) | 46(3) | 60(3) | 69(3) | 11(2) | −1(2) | −4(2) |
| C(32) | 41(2) | 48(2) | 42(2) | 4(2) | −4(2) | −4(2) |
| C(33) | 65(3) | 49(2) | 45(2) | 2(2) | −9(2) | −6(2) |
| C(29) | 69(3) | 62(3) | 50(3) | −11(2) | 0(2) | 9(3) |
| C(35) | 83(4) | 41(2) | 50(2) | −2(2) | −2(2) | 9(2) |
| C(24) | 57(3) | 50(2) | 43(2) | 9(2) | −2(2) | −7(2) |
| C(23) | 65(3) | 70(3) | 52(3) | 16(2) | 5(2) | −20(3) |
| C(36) | 133(6) | 61(3) | 57(3) | 0(2) | −35(4) | 18(4) |
| C(21) | 87(5) | 76(4) | 78(4) | −15(3) | −4(3) | 10(3) |
| C(20) | 96(6) | 133(6) | 71(4) | −19(4) | 7(4) | −5(5) |
| C(38) | 590(40) | 68(5) | 193(13) | −24(6) | −300(20) | 51(11) |

Figure 4:
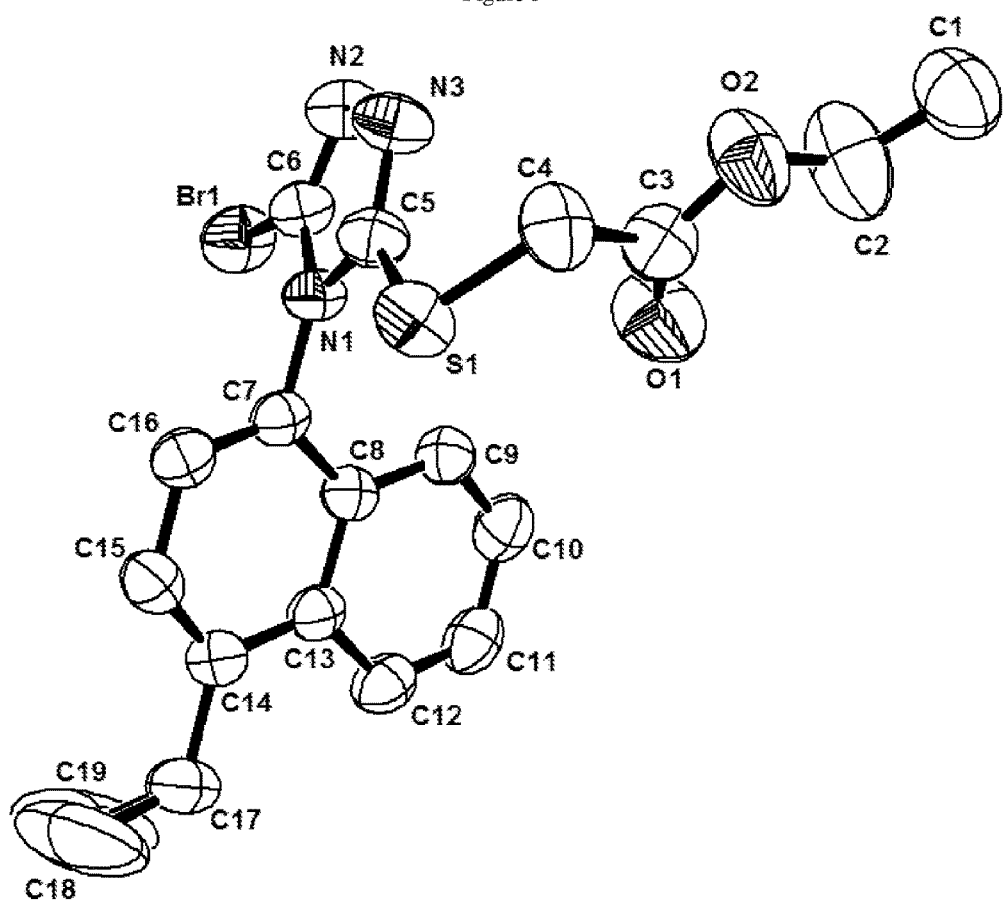
FIG. 4: The stereospecific ellipsoid of compound 12B single molecule.
Figure 5:
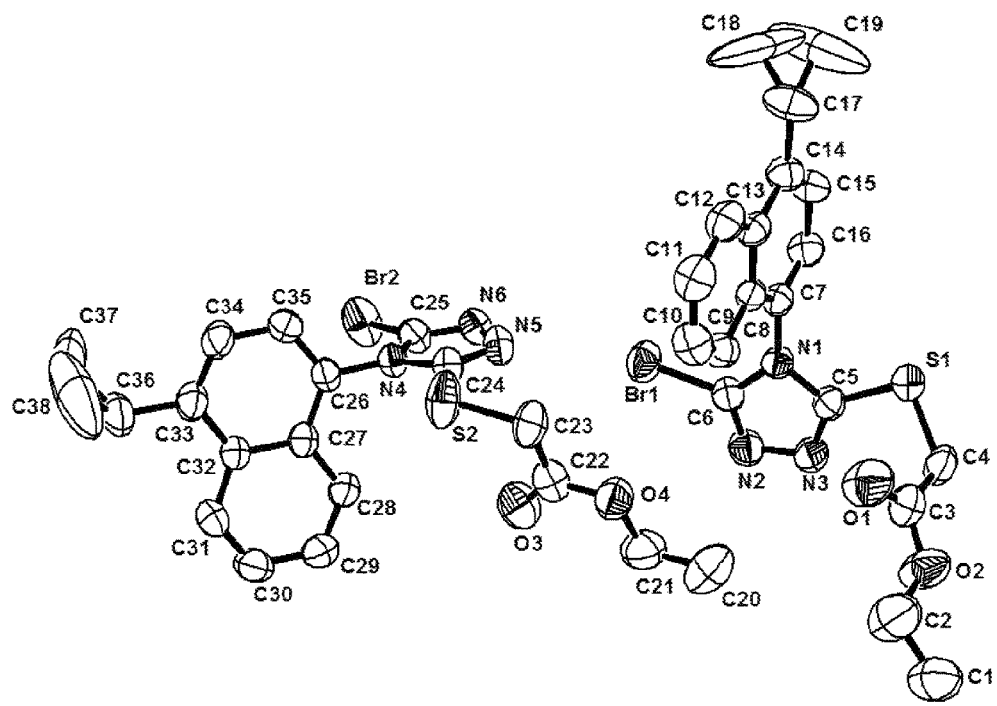
FIG. 5: The stereospecific ellipsoid of compound 12B bimolecular.
Figure 6:
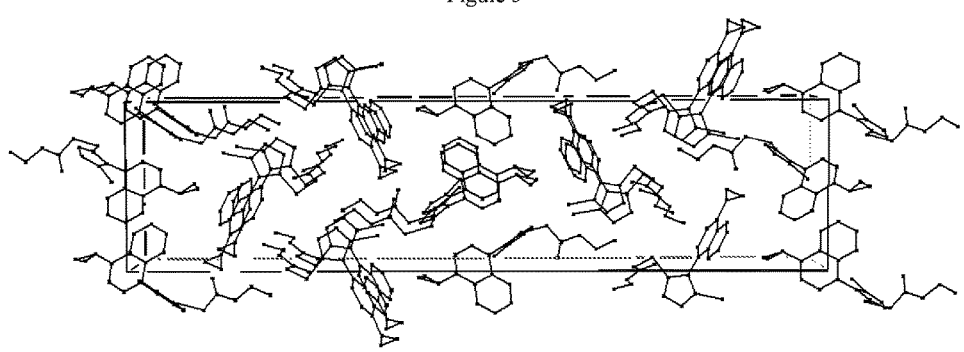
FIG. 6: The unit cell stacking diagram of compound 12B in the direction of a axis.

Compound 12B: $^1$H-NMR (400 MHz, DMSO-$d_6$, δ): 8.57 (d, J=8.4 Hz, 1H), 7.78-7.76 (m, 1H), 7.6 8-7.60 (m, 2H), 7.43 (d, J=8.0 Hz, 1H), 7.13 (d, J=8.0 Hz, 1H), 4.10-4.02 (m, 4H), 2.60-2.51 (m, 1H), 1.20-1.10 (m, 5H), 0.89-0.83 (m, 2H). SFC (chiral column: Chiralpak AS-H (250 mm×4.6 mm, 5 um); eluent: ethanol (0.05% DEA)/supercritical $CO_2$=5-40%; flow rate: 2.5 mL/min; detection way elength: 254 nm): $R_t$=5.11 min., e.e.=95.7%. $[α]^{25}_D$=−9.053 (c=8.645 mg/mL in ethanol). The si ngle crystal X-ray structure information of compound 12B was shown in FIG. 4-6 with detailed dat a below.

The Single Crystal X-ray Strucure Refinement Information of Compound 12B

| | |
|---|---|
| Identification code | 12B |
| Empirical formula | C19H18BrN3O2S |
| Formula weight | 432.33 |
| Temperature | 296(2) K |

| | |
|---|---|
| Wavelength | 1.54178 A |
| Crystal system, space group | Orthorhombic, P 21 21 21 |
| Unit cell dimensions | a = 7.29500(10) A  alpha = 90 deg. |
| | b = 11.3531(2) A  beta = 90 deg. |
| | c = 46.6392(6) A  gamma = 90 deg. |
| Volume | 3862.70(10) A^3 |
| Z, Calculated density | 8, 1.487 Mg/m^3 |
| Absorption coefficient | 4.063 mm −1 |
| F(000) | 1760 |
| Crystal size | 0.310 × 0.130 × 0.120 mm |
| Theta range for data collection | 3.791 to 67.336 deg. |
| Limiting indices | −8 <= h <= 8, −13 <= k <= 12, −43 <= l <= 55 |
| Reflections collected/unique | 18278/6680 [R(int) = 0.0417] |
| Completeness to theta = 67.336 | 98.1% |
| Refinement method | Full-matrix least-squares on F^2 |
| Data/restraints/parameters | 6680/0/470 |
| Goodness-of-fit on F^2 | 1.008 |
| Final R indices [I > 2sigma(I)] | R1 = 0.0417, wR2 = 0.1064 |
| R indices (all data) | R1 = 0.0498, wR2 = 0.1121 |
| Absolute structure parameter | 0.019(11) |
| Extinction coefficient | 0.00007(8) |
| Largest diff. peak and hole | 0.778 and −0.412 e · A^−3 |

Atomic Coordinate Parameters and Equivalent Temperature FactorValues of Compound 12B

| | x | y | z | U(eq) |
|---|---|---|---|---|
| Br(1) | 3762(1) | 2962(1) | 3573(1) | 70(1) |
| S(1) | 4995(3) | 5416(2) | 2569(1) | 64(1) |
| N(1) | 4337(6) | 4382(4) | 3082(1) | 45(1) |
| N(2) | 4347(8) | 2487(4) | 2989(1) | 61(1) |
| N(3) | 4691(8) | 3088(5) | 2734(1) | 62(1) |
| O(1) | 8937(9) | 4671(6) | 2656(1) | 97(2) |
| O(2) | 9164(8) | 3699(6) | 2246(1) | 90(2) |
| C(1) | 11938(12) | 2900(9) | 2087(2) | 94(3) |
| C(2) | 10987(14) | 3277(11) | 2333(2) | 115(4) |
| C(3) | 8322(10) | 4380(6) | 2429(1) | 64(2) |
| C(4) | 6470(9) | 4715(5) | 2311(1) | 65(2) |
| C(5) | 4671(8) | 4219(5) | 2797(1) | 50(1) |
| C(6) | 4156(8) | 3268(5) | 3184(1) | 49(1) |
| C(7) | 4246(7) | 5495(5) | 3229(1) | 43(1) |
| C(8) | 5768(7) | 5854(5) | 3397(1) | 42(1) |
| C(9) | 7357(8) | 5169(5) | 3433(1) | 51(1) |
| C(10) | 8775(8) | 5550(6) | 3599(1) | 62(2) |
| C(11) | 8686(9) | 6650(6) | 3731(1) | 62(2) |
| C(12) | 7180(9) | 7350(6) | 3700(1) | 57(2) |
| C(13) | 5658(7) | 6979(5) | 3532(1) | 45(1) |
| C(14) | 4077(8) | 7705(5) | 3492(1) | 52(1) |
| C(15) | 2689(9) | 7294(5) | 3323(1) | 57(2) |
| C(16) | 2758(8) | 6179(5) | 3192(1) | 53(1) |
| C(17) | 3971(11) | 8894(6) | 3626(2) | 78(2) |
| C(18) | 2820(30) | 9206(14) | 3839(4) | 277(17) |
| C(19) | 2460(20) | 9621(13) | 3602(5) | 226(13) |
| Br(2) | 1665(1) | 256(1) | 4746(1) | 87(1) |
| S(2) | 8133(2) | 2140(2) | 4362(1) | 78(1) |
| O(3) | 7655(8) | 597(5) | 3834(1) | 83(2) |
| O(4) | 8554(7) | 1984(4) | 3522(1) | 70(1) |
| N(4) | 5099(6) | 1170(4) | 4585(1) | 46(1) |
| N(5) | 4491(8) | 2194(5) | 4196(1) | 59(1) |
| N(6) | 2862(7) | 1712(5) | 4295(1) | 55(1) |
| C(20) | 9099(14) | 1738(9) | 3026(2) | 101(3) |
| C(21) | 8300(13) | 1170(7) | 3284(2) | 81(2) |
| C(22) | 8154(9) | 1592(6) | 3784(1) | 61(2) |
| C(23) | 8403(10) | 2566(6) | 3994(1) | 64(2) |
| C(24) | 5789(8) | 1858(5) | 4372(1) | 50(1) |
| C(25) | 3267(8) | 1118(5) | 4525(1) | 52(1) |
| C(26) | 6039(7) | 663(5) | 4826(1) | 45(1) |
| C(27) | 6952(7) | −432(5) | 4790(1) | 43(1) |
| C(28) | 7013(8) | −1022(6) | 4527(1) | 53(1) |
| C(29) | 7874(9) | −2089(6) | 4504(1) | 63(2) |
| C(30) | 8706(9) | −2606(6) | 4744(1) | 64(2) |
| C(31) | 8694(8) | −2041(5) | 5000(1) | 56(1) |
| C(32) | 7821(7) | −931(5) | 5036(1) | 43(1) |
| C(33) | 7790(9) | −322(6) | 5303(1) | 55(1) |
| C(34) | 6944(11) | 736(6) | 5317(1) | 65(2) |
| C(35) | 6052(11) | 1242(5) | 5080(1) | 61(2) |
| C(36) | 8693(14) | −842(7) | 5563(1) | 85(3) |
| C(37) | 8160(20) | −526(18) | 5844(2) | 173(7) |
| C(38) | 9810(30) | −310(14) | 5750(4) | 248(14) |

Bond Length and Bond Angular Values of Bonded Atoms of Compound 12B

| | |
|---|---|
| Br(1)—C(6) | 1.870(5) |
| S(1)—C(5) | 1.741(6) |
| S(1)—C(4) | 1.799(6) |
| N(1)—C(6) | 1.358(7) |
| N(1)—C(5) | 1.367(7) |
| N(1)—C(7) | 1.439(7) |
| N(2)—C(6) | 1.279(7) |
| N(2)—N(3) | 1.393(7) |
| N(3)—C(5) | 1.316(8) |
| O(1)—C(3) | 1.197(8) |
| O(2)—C(3) | 1.305(8) |
| O(2)—C(2) | 1.470(10) |
| C(1)—C(2) | 1.408(11) |
| C(1)—H(1A) | 0.9600 |
| C(1)—H(1B) | 0.9600 |
| C(1)—H(1C) | 0.9600 |
| C(2)—H(2A) | 0.9700 |
| C(2)—H(2B) | 0.9700 |
| C(3)—C(4) | 1.507(9) |
| C(4)—H(4A) | 0.9700 |
| C(4)—H(4B) | 0.9700 |
| C(7)—C(16) | 1.346(8) |
| C(7)—C(8) | 1.419(7) |
| C(8)—C(9) | 1.406(8) |
| C(8)—C(13) | 1.426(7) |
| C(9)—C(10) | 1.361(8) |
| C(9)—H(9) | 0.9300 |
| C(10)—C(11) | 1.395(9) |
| C(10)—H(10) | 0.9300 |
| C(11)—C(12) | 1.364(9) |
| C(11)—H(11) | 0.9300 |
| C(12)—C(13) | 1.423(8) |
| C(12)—H(12) | 0.9300 |
| C(13)—C(14) | 1.429(8) |
| C(14)—C(15) | 1.365(8) |
| C(14)—C(17) | 1.488(9) |
| C(15)—C(16) | 1.407(8) |
| C(15)—H(15) | 0.9300 |
| C(16)—H(16) | 0.9300 |
| C(17)—C(18) | 1.347(14) |
| C(17)—C(19) | 1.380(14) |
| C(17)—H(17) | 0.9800 |
| C(18)—C(19) | 1.23(3) |
| C(18)—H(18A) | 0.9700 |
| C(18)—H(18B) | 0.9700 |
| C(19)—H(19A) | 0.9700 |
| C(19)—H(19B) | 0.9700 |
| Br(2)—C(25) | 1.842(6) |
| S(2)—C(24) | 1.740(6) |
| S(2)—C(23) | 1.794(6) |
| O(3)—C(22) | 1.210(8) |
| O(4)—C(22) | 1.331(8) |
| O(4)—C(21) | 1.458(8) |
| N(4)—C(24) | 1.359(7) |
| N(4)—C(25) | 1.366(7) |
| N(4)—C(26) | 1.437(6) |
| N(5)—C(24) | 1.310(7) |
| N(5)—N(6) | 1.388(7) |
| N(6)—C(25) | 1.300(7) |
| C(20)—C(21) | 1.482(11) |
| C(20)—H(20A) | 0.9600 |

| | |
|---|---|
| C(20)—H(20B) | 0.9600 |
| C(20)—H(20C) | 0.9600 |
| C(21)—H(21A) | 0.9700 |
| C(21)—H(21B) | 0.9700 |
| C(22)—C(23) | 1.490(9) |
| C(23)—H(23A) | 0.9700 |
| C(23)—H(23B) | 0.9700 |
| C(26)—C(35) | 1.356(8) |
| C(26)—C(27) | 1.420(8) |
| C(27)—C(28) | 1.398(7) |
| C(27)—C(32) | 1.427(7) |
| C(28)—C(29) | 1.369(9) |
| C(28)—H(28) | 0.9300 |
| C(29)—C(30) | 1.403(9) |
| C(29)—H(29) | 0.9300 |
| C(30)—C(31) | 1.355(8) |
| C(30)—H(30) | 0.9300 |
| C(31)—C(32) | 1.422(8) |
| C(31)—H(31) | 0.9300 |
| C(32)—C(33) | 1.425(8) |
| C(33)—C(34) | 1.352(9) |
| C(33)—C(36) | 1.500(8) |
| C(34)—C(35) | 1.406(9) |
| C(34)—H(34) | 0.9300 |
| C(35)—H(35) | 0.9300 |
| C(36)—C(38) | 1.337(15) |
| C(36)—C(37) | 1.414(14) |
| C(36)—H(36) | 0.9800 |
| C(37)—C(38) | 1.30(3) |
| C(37)—H(37A) | 0.9700 |
| C(37)—H(37B) | 0.9700 |
| C(38)—H(38A) | 0.9700 |
| C(38)—H(38B) | 0.9700 |
| C(5)—S(1)—C(4) | 98.3(3) |
| C(6)—N(1)—C(5) | 103.4(4) |
| C(6)—N(1)—C(7) | 130.2(4) |
| C(5)—N(1)—C(7) | 126.3(4) |
| C(6)—N(2)—N(3) | 106.7(5) |
| C(5)—N(3)—N(2) | 106.7(4) |
| C(3)—O(2)—C(2) | 116.0(6) |
| C(2)—C(1)—H(1A) | 109.5 |
| C(2)—C(1)—H(1B) | 109.4 |
| H(1A)—C(1)—H(1B) | 109.5 |
| C(2)—C(1)—H(1C) | 109.5 |
| H(1A)—C(1)—H(1C) | 109.5 |
| H(1B)—C(1)—H(1C) | 109.5 |
| C(1)—C(2)—O(2) | 108.7(7) |
| C(1)—C(2)—H(2A) | 109.9 |
| O(2)—C(2)—H(2A) | 109.9 |
| C(1)—C(2)—H(2B) | 110.0 |
| O(2)—C(2)—H(2B) | 110.0 |
| H(2A)—C(2)—H(2B) | 108.3 |
| O(1)—C(3)—O(2) | 124.4(7) |
| O(1)—C(3)—C(4) | 126.0(7) |
| O(2)—C(3)—C(4) | 109.5(5) |
| C(3)—C(4)—S(1) | 113.9(4) |
| C(3)—C(4)—H(4A) | 108.8 |
| S(1)—C(4)—H(4A) | 108.8 |
| C(3)—C(4)—H(4B) | 108.8 |
| S(1)—C(4)—H(4B) | 108.8 |
| H(4A)—C(4)—H(4B) | 107.7 |
| N(3)—C(5)—N(1) | 110.5(5) |
| N(3)—C(5)—S(1) | 128.7(4) |
| N(1)—C(5)—S(1) | 120.9(4) |
| N(2)—C(6)—N(1) | 112.7(5) |
| N(2)—C(6)—Br(1) | 125.4(4) |
| N(1)—C(6)—Br(1) | 121.9(4) |
| C(16)—C(7)—C(8) | 122.4(5) |
| C(16)—C(7)—N(1) | 118.9(5) |
| C(8)—C(7)—N(1) | 118.6(5) |
| C(9)—C(8)—C(7) | 123.5(5) |
| C(9)—C(8)—C(13) | 119.3(5) |
| C(7)—C(8)—C(13) | 117.2(5) |
| C(10)—C(9)—C(8) | 121.3(6) |
| C(10)—C(9)—H(9) | 119.4 |
| C(8)—C(9)—H(9) | 119.4 |
| C(9)—C(10)—C(11) | 120.0(6) |
| C(9)—C(10)—H(10) | 120.0 |
| C(11)—C(10)—H(10) | 120.0 |
| C(12)—C(11)—C(10) | 120.8(6) |
| C(12)—C(11)—H(11) | 119.7 |
| C(10)—C(11)—H(11) | 119.6 |
| C(11)—C(12)—C(13) | 121.0(6) |
| C(11)—C(12)—H(12) | 119.5 |
| C(13)—C(12)—H(12) | 119.5 |
| C(8)—C(13)—C(12) | 117.6(5) |
| C(8)—C(13)—C(14) | 120.4(5) |
| C(12)—C(13)—C(14) | 122.0(5) |
| C(15)—C(14)—C(13) | 118.4(5) |
| C(15)—C(14)—C(17) | 120.9(6) |
| C(13)—C(14)—C(17) | 120.7(6) |
| C(14)—C(15)—C(16) | 122.1(6) |
| C(14)—C(15)—H(15) | 119.0 |
| C(16)—C(15)—H(15) | 118.9 |
| C(7)—C(16)—C(15) | 119.5(5) |
| C(7)—C(16)—H(16) | 120.2 |
| C(15)—C(16)—H(16) | 120.3 |
| C(18)—C(17)—C(19) | 53.6(12) |
| C(18)—C(17)—C(14) | 125.5(9) |
| C(19)—C(17)—C(14) | 123.3(9) |
| C(18)—C(17)—H(17) | 113.6 |
| C(19)—C(17)—H(17) | 113.9 |
| C(14)—C(17)—H(17) | 113.8 |
| C(19)—C(18)—C(17) | 64.6(10) |
| C(19)—C(18)—H(18A) | 117.0 |
| C(17)—C(18)—H(18A) | 117.3 |
| C(19)—C(18)—H(18B) | 117.3 |
| C(17)—C(18)—H(18B) | 117.5 |
| H(18A)—C(18)—H(18B) | 114.3 |
| C(18)—C(19)—C(17) | 61.8(10) |
| C(18)—C(19)—H(19A) | 117.5 |
| C(17)—C(19)—H(19A) | 117.4 |
| C(18)—C(19)—H(19B) | 117.9 |
| C(17)—C(19)—H(19B) | 117.5 |
| H(19A)—C(19)—H(19B) | 114.7 |
| C(24)—S(2)—C(23) | 100.5(3) |
| C(22)—O(4)—C(21) | 117.3(6) |
| C(24)—N(4)—C(25) | 103.8(5) |
| C(24)—N(4)—C(26) | 128.6(5) |
| C(25)—N(4)—C(26) | 127.5(5) |
| C(24)—N(5)—N(6) | 107.2(4) |
| C(25)—N(6)—N(5) | 106.5(5) |
| C(21)—C(20)—H(20A) | 109.5 |
| C(21)—C(20)—H(20B) | 109.4 |
| H(20A)—C(20)—H(20B) | 109.5 |
| C(21)—C(20)—H(20C) | 109.5 |
| H(20A)—C(20)—H(20C) | 109.5 |
| H(20B)—C(20)—H(20C) | 109.5 |
| O(4)—C(21)—C(20) | 107.0(7) |
| O(4)—C(21)—H(21A) | 110.3 |
| C(20)—C(21)—H(21A) | 110.4 |
| O(4)—C(21)—H(21B) | 110.3 |
| C(20)—C(21)—H(21B) | 110.3 |
| H(21A)—C(21)—H(21B) | 108.6 |
| O(3)—C(22)—O(4) | 123.8(7) |
| O(3)—C(22)—C(23) | 127.0(6) |
| O(4)—C(22)—C(23) | 109.2(5) |
| C(22)—C(23)—S(2) | 114.6(4) |
| C(22)—C(23)—H(23A) | 108.6 |
| S(2)—C(23)—H(23A) | 108.6 |
| C(22)—C(23)—H(23B) | 108.6 |
| S(2)—C(23)—H(23B) | 108.6 |
| H(23A)—C(23)—H(23B) | 107.6 |
| N(5)—C(24)—N(4) | 110.9(5) |
| N(5)—C(24)—S(2) | 129.8(4) |
| N(4)—C(24)—S(2) | 119.3(4) |
| N(6)—C(25)—N(4) | 111.6(5) |
| N(6)—C(25)—Br(2) | 126.4(5) |
| N(4)—C(25)—Br(2) | 121.9(4) |
| C(35)—C(26)—C(27) | 121.6(5) |
| C(35)—C(26)—N(4) | 119.6(5) |
| C(27)—C(26)—N(4) | 118.9(4) |
| C(28)—C(27)—C(26) | 122.5(5) |
| C(28)—C(27)—C(32) | 120.0(5) |
| C(26)—C(27)—C(32) | 117.5(5) |
| C(29)—C(28)—C(27) | 120.5(5) |
| C(29)—C(28)—H(28) | 119.8 |
| C(27)—C(28)—H(28) | 119.7 |

| | |
|---|---|
| C(28)—C(29)—C(30) | 120.4(6) |
| C(28)—C(29)—H(29) | 119.8 |
| C(30)—C(29)—H(29) | 119.8 |
| C(31)—C(30)—C(29) | 120.2(6) |
| C(31)—C(30)—H(30) | 119.9 |
| C(29)—C(30)—H(30) | 119.9 |
| C(30)—C(31)—C(32) | 121.7(5) |
| C(30)—C(31)—H(31) | 119.2 |
| C(32)—C(31)—H(31) | 119.1 |
| C(31)—C(32)—C(33) | 122.6(5) |
| C(31)—C(32)—C(27) | 117.2(5) |
| C(33)—C(32)—C(27) | 120.2(5) |
| C(34)—C(33)—C(32) | 118.8(5) |
| C(34)—C(33)—C(36) | 120.7(6) |
| C(32)—C(33)—C(36) | 120.5(6) |
| C(33)—C(34)—C(35) | 122.3(5) |
| C(33)—C(34)—H(34) | 118.8 |
| C(35)—C(34)—H(34) | 118.8 |
| C(26)—C(35)—C(34) | 119.6(6) |
| C(26)—C(35)—H(35) | 120.2 |
| C(34)—C(35)—H(35) | 120.2 |
| C(38)—C(36)—C(37) | 56.4(11) |
| C(38)—C(36)—C(33) | 128.1(10) |
| C(37)—C(36)—C(33) | 121.9(9) |
| C(38)—C(36)—H(36) | 113.4 |
| C(37)—C(36)—H(36) | 112.1 |
| C(33)—C(36)—H(36) | 113.0 |
| C(38)—C(37)—C(36) | 58.8(9) |
| C(38)—C(37)—H(37A) | 116.7 |
| C(36)—C(37)—H(37A) | 117.5 |
| C(38)—C(37)—H(37B) | 118.4 |
| C(36)—C(37)—H(37B) | 118.8 |
| H(37A)—C(37)—H(37B) | 115.1 |
| C(36)—C(38)—C(37) | 64.7(11) |
| C(36)—C(38)—H(38A) | 117.0 |
| C(37)—C(38)—H(38A) | 118.6 |
| C(36)—C(38)—H(38B) | 116.7 |
| C(37)—C(38)—H(38B) | 116.8 |
| H(38A)—C(38)—H(38B) | 114.3 |

Anisotropic Temperature Factors Values of Compound 12B

| | U11 | U22 | U33 | U23 | U13 | U12 |
|---|---|---|---|---|---|---|
| Br(1) | 89(1) | 64(1) | 56(1) | 10(1) | 10(1) | −13(1) |
| S(1) | 83(1) | 58(1) | 50(1) | 7(1) | 6(1) | 10(1) |
| N(1) | 54(3) | 39(3) | 42(2) | −4(2) | −1(2) | −6(2) |
| N(2) | 77(4) | 49(3) | 56(3) | −1(2) | −8(3) | −3(2) |
| N(3) | 86(4) | 53(3) | 47(2) | −9(2) | −6(2) | 3(3) |
| O(1) | 96(4) | 125(5) | 69(3) | −26(3) | −26(3) | 19(4) |
| O(2) | 72(3) | 136(5) | 61(3) | −29(3) | −12(3) | 30(3) |
| C(1) | 81(5) | 107(7) | 95(5) | −18(5) | −4(4) | 21(5) |
| C(2) | 84(6) | 187(11) | 74(5) | −10(6) | −15(5) | 52(7) |
| C(3) | 69(4) | 75(4) | 47(3) | 2(3) | −3(3) | −3(3) |
| C(4) | 69(4) | 88(5) | 37(3) | 5(3) | 3(3) | 6(4) |
| C(5) | 62(3) | 49(3) | 40(3) | −4(2) | −9(2) | 1(3) |
| C(6) | 54(3) | 45(3) | 47(3) | −1(2) | −5(2) | −5(2) |
| C(7) | 48(3) | 43(3) | 38(2) | 1(2) | 2(2) | −6(2) |
| C(8) | 47(3) | 42(3) | 36(2) | 1(2) | 2(2) | −1(2) |
| C(9) | 52(3) | 47(3) | 55(3) | 0(2) | 4(3) | 0(3) |
| C(10) | 49(3) | 66(4) | 70(3) | 8(3) | −5(3) | −4(3) |
| C(11) | 49(3) | 78(5) | 59(3) | −2(3) | −10(3) | −12(3) |
| C(12) | 61(4) | 62(4) | 49(3) | −7(3) | −2(3) | −14(3) |
| C(13) | 49(3) | 46(3) | 40(2) | −2(2) | 5(2) | −7(2) |
| C(14) | 52(3) | 45(3) | 58(3) | −6(2) | 2(3) | −5(3) |
| C(15) | 54(3) | 50(4) | 68(4) | −7(3) | 0(3) | 9(3) |
| C(16) | 51(3) | 54(4) | 53(3) | −7(3) | −6(3) | −5(3) |
| C(17) | 68(4) | 47(4) | 120(6) | −23(4) | −11(4) | 0(3) |
| C(18) | 410(40) | 105(12) | 310(20) | −122(14) | 280(30) | −77(16) |
| C(19) | 169(14) | 90(10) | 420(30) | −110(16) | −150(20) | 71(11) |
| Br(2) | 52(1) | 102(1) | 107(1) | 44(1) | 4(1) | −9(1) |
| S(2) | 62(1) | 115(2) | 58(1) | 28(1) | −11(1) | −31(1) |
| O(3) | 88(4) | 65(3) | 96(4) | 14(3) | 0(3) | −13(3) |
| O(4) | 83(3) | 68(3) | 59(2) | 2(2) | 5(2) | −5(3) |
| N(4) | 51(2) | 45(3) | 41(2) | 7(2) | −1(2) | 1(2) |
| N(5) | 68(3) | 59(3) | 50(2) | 13(2) | −8(2) | 0(3) |
| N(6) | 52(3) | 54(3) | 59(3) | 8(2) | −7(2) | 3(2) |
| C(20) | 100(6) | 135(8) | 70(5) | −17(5) | 8(5) | −8(6) |
| C(21) | 88(5) | 79(5) | 76(4) | −15(4) | −2(4) | 10(4) |
| C(22) | 51(3) | 62(4) | 70(4) | 12(3) | −4(3) | −6(3) |
| C(23) | 69(4) | 70(4) | 52(3) | 12(3) | 4(3) | −23(3) |
| C(24) | 54(3) | 51(3) | 45(3) | 8(2) | −3(2) | −4(3) |
| C(25) | 48(3) | 50(3) | 57(3) | 7(2) | −1(3) | 3(3) |
| C(26) | 45(3) | 46(3) | 43(3) | 7(2) | −1(2) | 2(2) |
| C(27) | 44(2) | 44(3) | 41(3) | 5(2) | −1(2) | −8(2) |
| C(28) | 56(3) | 61(4) | 40(3) | 0(2) | −3(2) | 5(3) |
| C(29) | 69(4) | 66(4) | 54(3) | −10(3) | 0(3) | 11(3) |
| C(30) | 65(4) | 56(4) | 71(4) | −7(3) | −4(3) | 14(3) |
| C(31) | 54(3) | 55(3) | 58(3) | 7(3) | −11(3) | 5(3) |
| C(32) | 45(3) | 44(3) | 40(3) | 2(2) | −4(2) | −3(2) |
| C(33) | 68(3) | 53(4) | 43(3) | 2(2) | −11(3) | −6(3) |
| C(34) | 104(5) | 48(4) | 43(3) | −7(2) | −14(3) | 2(3) |
| C(35) | 87(5) | 42(3) | 52(3) | −1(2) | −2(3) | 11(3) |
| C(36) | 136(8) | 61(4) | 59(4) | −4(3) | −40(5) | 22(5) |
| C(37) | 163(13) | 300(20) | 56(5) | 49(7) | 3(7) | 77(14) |
| C(38) | 410(30) | 93(10) | 240(20) | −4(12) | −260(20) | 14(16) |

Step 2: Preparation of Compound (−)-Lesinurad

Compound 12A (106.00 mg, 245.18 μmol, 1.00 eq) was dissolved in THF/water/ethanol (3 mL, 1:1:1). After cooling to 0° C., LiOH.H$_2$O (12.35 mg, 294.22 μmol, 1.20 eq) was added and the mixture was stirred at 0° C. for 1 hour. After the reaction, aqueous HCl solution (1 mol/L) was added to adjust pH=4. The THF and ethanol were removed under nitrogen flow at room temperature and water (1 mL) was added. The aqueous solution was extracted with DCM (2 mL×6). The organic phase were combined and the DCM was removed under nitrogen flow at room temperature. Ethanol (1 mL) was added to dissolve the residue and water (10 mL) was then added, the mixture was lyophilized to give (−)-Lesinurad (94.40 mg, 233.50 μmop as white solid. $^1$H-NMR (400 MHz, DMSO-d$_6$, δ): 8.59 (d, J=8.4 Hz, 1H), 7.79-7.71 (t, J=7.6 Hz, 1H), 7.70-7.61 (m, 2H), 7.45 (d, J=8.0 Hz, 1H), 7.16 (d, J=8.4 Hz, 1H), 3.97 (s, 2H), 2.60-2.55 (m, 1H), 1.18-1.14 (d, J=6.4 Hz, 2H), 0.91-0.86 (m, 2H). LC/MS (chromatographic column: Ultimate XB-C18, 3 μm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) R$_t$=0.801 min; MS m/z: 404 [M+H]$^+$, 406 [M+H+2]$^+$. SFC (chiral column: Chiralpak AS-H (250 mm×4.6 mm, 5 μm); eluent: A: supercritical CO$_2$, B: Methanol (0.05% DEA); gradient: 5-40% B (5 min), 40% B (3 min), 5% B (1.5 min); flow rate: 2.5 mL/min; column temperature: 35° C.): R$_t$=5.197 min. e.e. =96.5%. [α]$^{22}_D$=−3.693 (c=3.030 mg/mL in ethanol).

Step 3: Preparation of Compound (+)-Lesinurad

Compound 12B (45.00 mg, 104.09 μmol, 1 eq) was dissolved in THF/water/ethanol (3 mL, 1:1:1). After cooling to 0° C., LiOH.H$_2$O (5.24 mg, 124.9 μmol, 1.20 eq) was added and the mixture was stirred at 0° C. for 1 hour. After the reaction, aqueous HCl solution (1 mol/L) was added to adjust pH=4. The THF and ethanol were removed under nitrogen flow at room temperature and water (1 mL) was added. The aqueous solution was extracted with DCM (2 mL×6). The organic phase were combined and the DCM was removed under nitrogen flow at room temperature. Ethanol (1 mL) was added to dissolve the residue and water (10 mL) was then added, the mixture was lyophilized to give (+)-Lesinurad (38.40 mg, 82.59 μmop as white solid. $^1$H-NMR (400 MHz, DMSO-d$_6$, δ): 8.59 (d, J=8.4 Hz, 1H), 7.80-7.72

(t, J=7.2 Hz, 1H), 7.71-7.61 (m, 2H), 7.45 (d, J=7.2 Hz, 1H), 7.16 (d, J=8.0 Hz, 1H), 3.99 (s, 2H), 2.60-2.55 (m, 1H), 1.20-1.12 (dd, J=8.4 Hz, J=1.6 Hz, 2H), 0.91-0.83 (m, 2H). LC/MS (chromatographic column: Ultimate XB-C18, 3 μm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) $R_t$=0.796 min; MS m/z: 404 [M+H]$^+$, 406 [M+H+2]$^+$. SFC (chiral column: Chiralpak AS-H (250 mm×4.6 mm, 5 μm); eluent: A: supercritical $CO_2$, B: Methanol (0.05% DEA); gradient: 5-40% B (5 min), 40% B (3 min), 5% B (1.5 min); flow rate: 2.5 mL/min; column temperature: 35° C.): $R_t$=5.570 min. e.e. =95.9%. $[\alpha]^{25}_D$=4.432 (c=3.35 mg/mL in ethanol)

Example 2: Preparation of (−)-Lesinurad and (+)-Lesinurad

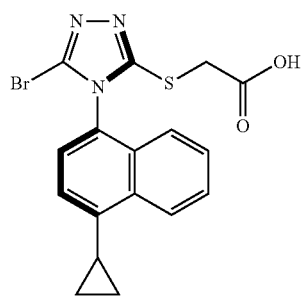

(+)-Lesinurad

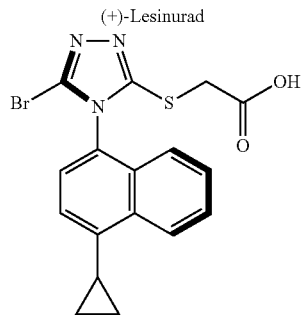

(−)-Lesinurad

Synthetic Route:

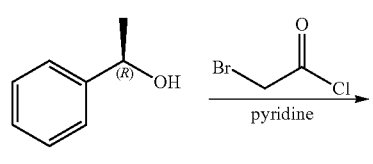

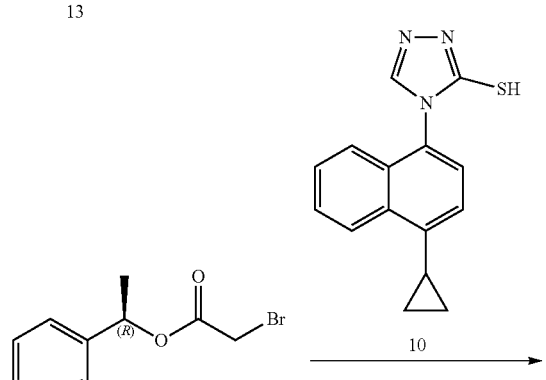

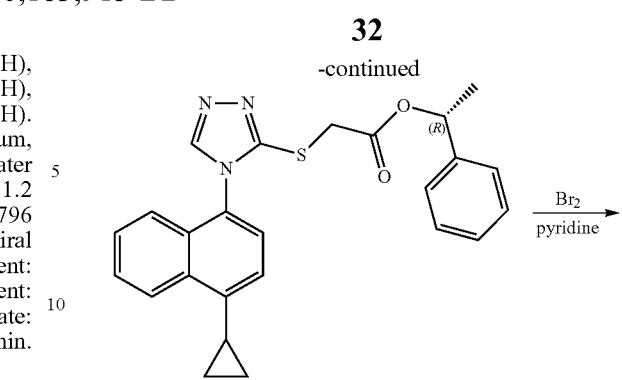

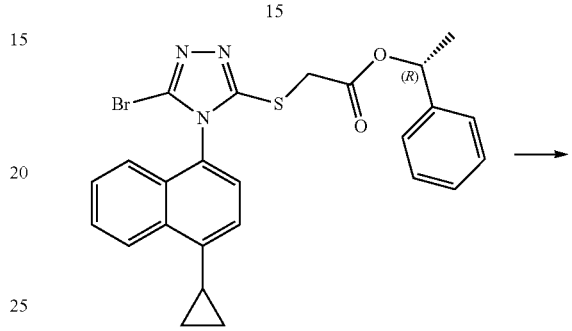

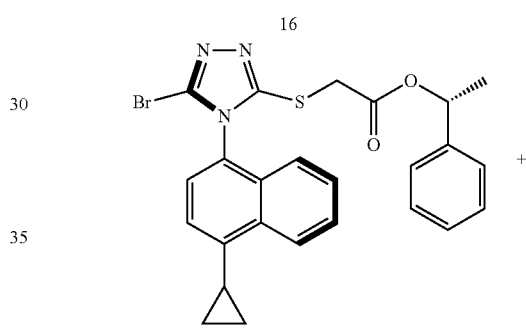

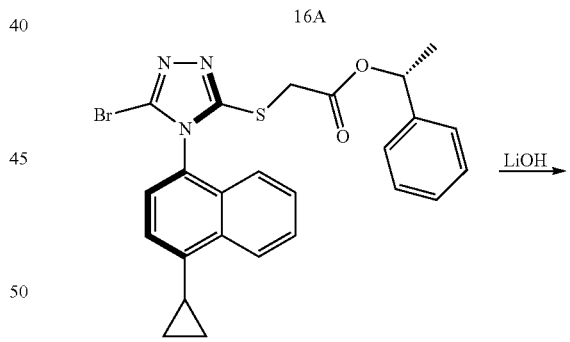

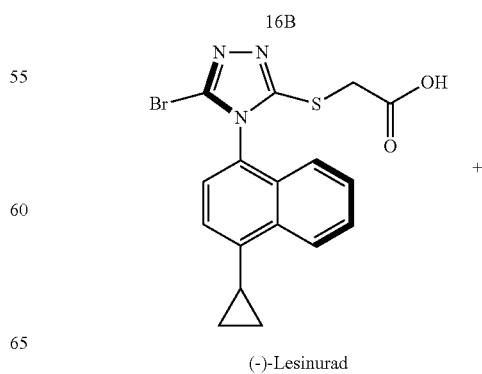

(−)-Lesinurad

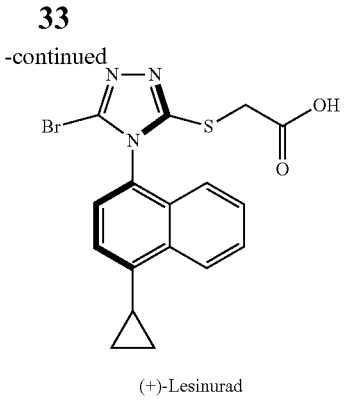

(+)-Lesinurad

Step 1: Preparation of Compound 14

A solution of compound 13 (2.00 g, 16.37 mmol, 1.00 eq) and pyridine (2.59 g, 32.74 mmol, 2.00 eq) in toluene (30.00 mL) was cooled to 0° C. under an ice bath, 2-bromoacetyl chloride (3.09 g, 19.64 mmol) was added and the mixture was stirred at 0° C. for 1 h, a large number of white solid was precipitated. After the reaction, the mixture was filtered, the filtrate cake was washed with dichloromethane (3 mL). The resulting filtrate was evaporated to dryness to give a yellow oil crude, which was purified by column chromatography (eluting with 0-15% ethyl acetate/petroleum ether) to give compound 14 as colorless oil (3.20 g, 13.16 mmol, 80.41% yield). $^1$H-NMR (400 MHz, CDCl$_3$, δ): 7.45-7.22 (m, 6H), 6.00-5.92 (m, 1H), 4.07 (s, 1H), 3.85 (s, 1H), 1.63-1.55 (d, J=4 Hz, 3H).

Step 2: Preparation of Compound 15

Compound 10 was prepared according to the method disclosed in patent application CN10352440A. A mixture of compound 10 (50.00 mg, 187.02 µmol, 1.00 eq), compound 14 (54.56 mg, 224.42 µma 1.20 eq) and K$_2$CO$_3$ (31.02 mg, 224.42 µmol, 1.20 eq) dissolved in DMF (10 mL) was stirred at 15° C. for 2.5 h. After the reaction, the mixture was concentrated to dryness to give a yellow solid crude, which was purified by thin-layer chromatography PTLC (eluting with 50% ethyl acetate/petroleum ether) to give 15 (1.4 g, 87%) as colorless oil. LC/MS (chromatographic column: Ultimate XB-C18, 3 µm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) $R_t$=0.888 min, MS m/z: 431[M+H]$^+$. SFC (chiral column: Chiralpak AD-3 (150 mm×4.6 mm T.D., 3 µm; eluent: A: supercriticalCO$_2$, B: isopropanol (0.05% DEA); gradient: 5-40% B (5 min), 40% B (3 min), 5% B (2.5 min); flow rate: 2.5 mL/min; column temperature: 35° C.; detection wavelength: 254 nm) $R_t$=5.766 min.

Step 3: Preparation of Compound 16A and 16B

A solution of compound 15 (1.30 g, 3.03 mmol, 1.00 eq) and pyridine (287.61 mg, 3.64 mmol, 1.20 eq) in acetonitrile (500 mL) was cooled to 0° C. under an ice bath, bromide (1.45 g, 9.09 mmol, 3.00 eq) was added and the mixture was warmed to 15° C. and stirred for 4 hours. The reaction was quenched with 20 mL of saturated aqueous NaHSO$_3$ solution. The solvent was removed under reduced pressure to give crude compound 16 as yellow solid. The crude product 16 was purified by flash column chromatography Combi Flash (eluting with 0-20% ethyl acetate/petroleum ether) to give compound 16A and 16B.

Compound 16A: LC/MS (chromatographic column: Ultimate XB-C18, 3 µm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) $R_t$=0.951 min, MS: m/z 508 [M+H]$^+$, 510 [M+H+2]$^+$. SFC (chiral column: Chiralcel OJ-H 250×4.6 mm I.D., 5 µm; eluent: isopropanol (0.05% DEA)/supercritical CO$_2$ (5%-40%); flow rate: 2.4 mL/min; detection wavelength: 220 nm) $R_t$=8.41 min.

Compound 16B: LC/MS (chromatographic column: Ultimate XB-C18, 3 µm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) $R_t$=0.946 min, MS: m/z 508 [M+H]$^+$, 510 [M+H+2]$^+$. SFC (chiral column: Chiralcel OJ-H 250×4.6 mm I.D., 5 µm; eluent: isopropanol (0.05% DEA)/supercritical CO$_2$, 5%-40%; flow rate: 2.4 mL/min; detection wavelength: 220 nm) $R_t$=7.54 min.

Step 4: Preparation of (−)-Lesinurad

A mixture of compound 16A (10.00 mg, 19.67 µmol, 1.00 eq) and LiOH.H$_2$O (1.65 mg, 39.34 µmol, 2.00 eq) in THF/water (1.50 mL/1.50 mL) was stirred at 15° C. for 16 hours. After the reaction, aqueous HCl solution (1 mol/L) was added to adjust the mixture to pH=2-3. The aqueous solution was evaporated to dryness to give a yellow oil crude, which was purified by preparative chromatography HPLC (preparative column: Phenomenex Synergi C18 150 mm×30 mm×4 µm; eluent: A: water (0.05% HCl), B: acetonitrile; gradient: 38-68% B (12 min); 100% B (2 min); flow rate: 25 mL/min) and evaporated to give compound (−)-Lesinurad as white solid. LC/MS (chromatographic column: Ultimate XB-C18, 3 µm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) $R_t$=0.786 min; MS m/z: 404 [M+H]$^+$, 406 [M+H+2]$^+$. SFC (chiral column: Chiralpak AS-H 250×4.6 mm I.D., 5 µm; eluent: A: supercritical CO$_2$, B: methanol (0.05% DEA); gradient: 5%-40% B (5 min), 40% B (3 min), 5%(1.5 min); flow rate: 2.5 mL/min; column temperature: 35° C.) $R_t$=5.279 min.

Step 5: Preparation of Compound (+)-Lesinurad

A mixture of compound 16B (10.00 mg, 19.67 µmol, 1.00 eq) and LiOH.H$_2$O (1.65 mg, 39.34 µmol, 2.00 eq) in THF/water (1.50 mL/1.50 mL) was stirred at 15° C. for 16 hours. After the reaction, aqueous HCl solution (1 mol/L) was added to adjust the mixture to pH=2-3. The aqueous solution was evaporated to dryness to give a yellow oil crude, which was purified by preparative chromatography HPLC (preparative column: Phenomenex Synergi C18 150 mm×30 mm×4 µm; eluent: A: acetonitrile, B: water (0.05% HCl); gradient: 38-68% A (12 min); 100% A (2 min); flow rate: 25 mL/min) and evaporated to give compound (+)-Lesinurad as white solid. LC/MS (chromatographic column: Ultimate XB-C18, 3 µm, 30×2.1 mm; eluent: acetonitrile (0.02% TFA) in water (0.04% TFA); gradient: 5-95% (1.5 min); flow rate: 1.2 mL/min; detection wavelength: 220 nm &254 nm) $R_t$=0.787 min; MS m/z: 404 [M+H]$^+$, 406 [M+H+2]$^+$. SFC (chiral column: Chiralpak AS-H 250×4.6 mm I.D., 5 µm; eluent: A: supercritical CO$_2$, B: methanol (0.05% DEA); gradient: 5%-40% B (5 min), 40% B (3 min), 5% (1.5 min); flow rate: 2.5 mL/min; column temperature: 35° C.) $R_t$=5.666 min.

Test 1: Evaluation of the Inhibitory Effects of the HEK293 Cell Line Stably Transfected with URAT1 Gene won the Transport of Labeled Uric Acid 1. Experimental Objective:

A HEK293 cell line stably transfected with URAT-1 (uric acid transporter) gene was used to determine the IC$_{50}$ value of the compound to inhibit the reabsorption of uric acid.

2. Experimental Material:

URAT-1 (HEK293) cell lines: HEK293 cell line with human URAT1 stable transfected (the cell line was constructed by WuXi AppTec in Shanghai).

Cell culture medium: DMEM culture (Invitrogen 11965118) containing 10% fetal bovine serum (PBS Corning 35076105), 1% Sodium Pyruvate (Invitrogen 113600070) and 300 μg/mL G418 (Gibco 10131).

HBSS buffer: (Invitrogen 14025126);

0.1 M NaOH solution: formulated from NaOH dry powder (Chinasun Specialty Products Co., Ltd. 20090206);

$^{14}$C-Uric acid solution (ARC 0513A);

$CO_2$ incubator: (Thermo);

Liquid scintillation counter Tricarb: (Beckman).

3. Experimental Procedures and Methods a Cells Inoculation:

1) The supernatant of cells cultured in T150 flask was discarded and cells were washed with 10 mL of PBS.

2) Pre-warmed 0.25% Trysin-EDTA was added to the washed cell culture flask, which was rotated to uniformly covered at the bottom by Trysin-EDTA. Digestion at room temperature.

3) Each T150 culture flask was suspended with 10-15 mL culture medium, 0.1 mL was absorbed and diluted with trypan blue solution, and the cells was 2 folds serial counted.

4) The cells were diluted with culture medium to $2.5 \times 10^5$ cells/mL. The diluted cells was seeded into 24-well plates (800 μg/hole, $2 \times 10^5$ cells/hole) coated with rat tail collagen and the plates were incubated at 37° C. under 5% $CO_2$ overnight.

b Cells Preparation

1) The cells were inoculated on the 24-well plates and discarded 16-18 hours later. Add 600 μL HBSS buffer to each hole and clean it two times 2) Absorb the HBSS buffer and then add 180 μL of HBSS buffer to each hole.

c Compound Solution Preparation, Dilution and Sample Addition

1) Dissolve the compound powder in 100% DMSO. The compound is then 3 folds serial diluted for 6 points, or 10 folds serial diluted for 2 points, with a maximum initial concentration of 50 mM.

2) Trasfer the 5 μL DMSO solution of step 1 into the 120 mL HBSS buffer and dilute it 25 times.

3) 10 μL dilutions of step 2 are added to a 24-well cell plate and incubated for 15 minutes in a 5% $CO_2$ incubator for 37° C. The final concentration of DMSO was 0.2%. Cell control hole: no compound, containing only 0.2% DMSO.

d Detection:

10 μL of $^{14}$C-Uric acid solution was diluted and added to each well of 24-well plates and the final concentration of $^{14}$C-uric acid was 50 μM. Plates were incubated at 37° C. under 5% $CO_2$ for 10 min. The supernatant in each well of 24-well plates was discarded, and the cells were washed with HBSS buffer twice. 0.1 M of NaOH solution was used to lyses the cells. Collect the cell lysis in liquid scintillation and read the Tri-Carb signal in liquid scintillation counter after adding the liquid scintillation solution.

e Data Processing and Analysis

Based on the luminescence data, the inhibitory effect of compounds on URAT-1 was analyzed, and the percentage of inhibition data was calculated. $IC_{50}$ value was obtained by GraphPad Prism software using non-linear curve fitting based on the percent inhibition (Inh %).

4. Results were Shown in Table 1:

TABLE 1

The $IC_{50}$ values of URAT-1 inhibitory effect for each examples

| | Test Compounds | $IC_{50}$ |
|---|---|---|
| 1 | (±)-Lesinurad | 11.66 μM (n = 3) |
| 2 | (+)-Lesinurad | 3.84 μM (n = 3) |
| 3 | (−)-Lesinurad | 17.21 μM (n = 3) |

The testing results shows: after multiple parallel tests, (+)-Lesinurad showed obviously higher in vitro potency than (−)-Lesinurad and (±)-Lesinurad, and was an atropisomer with higher in vitro potency.

Test 2: Evaluation of the Stability of Solid Compounds in Ambient Temperature.

Experimental Procedures and Methods:

20 mg of test compound was placed into 5 mL brown transparent sealed container with stopper and stoned in the nitrogen cabinet (15° C.) in the dark. After the preset storage time, about 2 mg of test compound was accurately weighed, added into ethanol to prepare 1 mg/mL ethanol solution. The purity and chiral purity of the compound was detected by high performance liquid chromatography (HPLC) or LC-MS (LCMS) and supercritical fluid chromatography (SFC). The experimental results was shown in Table 2:

TABLE 2

The Testing Results of Stability of Solid Compounds in Ambient Temperature

| Test Compounds | (+)-Lesinurad | | (−)-Lesinurad | |
|---|---|---|---|---|
| Storing Time | 0 day | >80 days | 0 day | >80 days |
| Enantiomer Excess of the Compound | 95.9% | Unchanged | 96.5% | Unchanged |

Note:
The same SFC analytic condition was used as the condition used in step 2 and 3 in test 1.

The data showed that the solid powder of (+)-Lesinurad and (−)-Lesinurad were very stable at 15° C. after storing over 80 days. No SFC purity change was observed, the solid still remains stable.

Test 3: Evaluation of the Stability of Compounds in Ethanol Solutions.

Experimental Procedures and Methods:

An appropriate amount of test compound was accurately weighed, added into ethanol to obtain an ethanol solution. The ethanol solution of the compound was stirred in a heated oil bath. At the end of the test, the purity and chiral purity of the compound was detected by high performance liquid chromatography (HPLC) or LC-MS (LCMS) and supercritical fluid chromatography (SFC). The experimental results were shown in Table 3:

TABLE 3

The Testing Results of Stability of Compounds in Ethanol Solutions

| Test Compounds | (+)-Lesinurad | | (−)-Lesinurad |
|---|---|---|---|
| Heating Temperature | 37° C. | 70° C. | 37° C. |

TABLE 3-continued

The Testing Results of Stability of Compounds in Ethanol Solutions

| Heating Time | 0 day | 3 days | 3 days | 0 day | 4 days | 7 days |
|---|---|---|---|---|---|---|
| Enantiomer Excess of Compound | 95.9% | Unchanged | Unchanged | 96.5% | Unchanged | Unchanged |

Note:
The same SFC analytic condition was used as the condition used in step 2 and 3 in test 1.

The data showed that the solid (+)-Lesinurad and (−)-Lesinurad were very stable in ethanol solutions after heating to 37° C. and even up to 70° C. No SFC purity change was observed, the solution still remains stable.

Example 4: Evaluation of the Stability of Compounds in DMSO Solutions

Experimental Procedures and Methods:

An appropriate amount of test compound was accurately weighed, added into DMSO to obtain a DMSO solution. The DMSO solution of the compound was stirred in a heated oil bath. At the end of the test, a sample amount of the DMSO solution was diluted with ethanol and the purity and chiral purity of the compound was detected by high performance liquid chromatography (HPLC) or LC-MS (LCMS) and supercritical fluid chromatography (SFC). The experimental results were shown in Table 4:

TABLE 4

The Testing Results of Stability of Compounds in Ethanol Solutions

| Test Compounds | (+)-Lesinurad | | | | | | |
|---|---|---|---|---|---|---|---|
| Heating Temperature | 80° C. | | | | | | |
| Heating Time | 0 h | 2 h | 4 h | 8 h | 24 h | 2 × 24 h | 4 × 24 h |
| Enantiomer Excess of Compound | 95.9% | Unchanged | Unchanged | Unchanged | Unchanged | Unchanged | Unchanged |
| Heating Temperature | 120° C. | | | | | | |
| Heating Time | 0 h | 2 h | 4 h | 8 h | 24 h | 2 × 24 h | 4 × 24 h |
| Enantiomer Excess of Compound | 95.9% | Unchanged | Unchanged | Unchanged | Unchanged | Unchanged | Unchanged |
| Heating Temperature | 160° C. | | | | | | |
| Heating Time | 0 h | 8 h | | | | | |
| Enantiomer Excess of Compound | 95.9% | Unchanged | | | | | |
| Test Compounds | (−)-Lesinurad | | | | | | |
| Heating Temperature | 80° C. | | | | | | |
| Heating Time | 0 h | 2 h | 4 h | 8 h | 24 h | 2 × 24 h | 4 × 24 h |
| Enantiomer Excess of Compound | 96.5% | Unchanged | Unchanged | Unchanged | Unchanged | Unchanged | Unchanged |
| Heating Temperature | 120° C. | | | | | | |

TABLE 4-continued

The Testing Results of Stability of Compounds in Ethanol Solutions

| Heating Time | 0 h | 2 h | 4 h | 8 h | 24 h | 2 × 24 h | 4 × 24 h |
|---|---|---|---|---|---|---|---|
| Enantiomer Excess of Compound | 96.5% | Unchanged | Unchanged | Unchanged | Unchanged | Unchanged | Unchanged |
| Heating Temperature | | | | 160° C. | | | |
| Heating Time | 0 h | 8 h | | | | | |
| Enantiomer Excess of Compound | 96.5% | Unchanged | | | | | |

Note:
The same SFC analytic condition was used as the condition used in step 1 and 2 in test 1.

The data showed that the solid (+)-Lesinurad and (−)-Lesinurad were very stable in DMSO solutions after heating to 80° C., 120° C. and even up to 160° C. No SFC purity change was observed, the solution still remains stable.

Test 5: Evaluation of the Stability of Compounds in Rat Plasma and Human Plasma

1. Experimental Materials
    1.1 Test Compound working solutions
    (+)-Lesinurad and (−)-Lesinurad
    1.2 Test Matrix

| Species/ Matrix | Minimum No. of Individuals | Anticoagulant Used | Supplier | Cat# | Batch |
|---|---|---|---|---|---|
| Human Plasma | 3 Male & 3 Female | EDTA-$K_2$ | Bioreclamation IVT | $HMPLEDTA_2$ | BRH855151 |
| SD Rat Plasma | 10 Male | EDTA-$K_2$ | Bioreclamation IVT | $RATPLEDTA_2$-M | RAT233103 |

2. Experimental Procedures and Methods
    2.1 Prior to the experiment, the frozen plasma stored at −40° C. was thawed at room temperature and incubated in a 37° C. water bath for 5-10 min; centrifuged at 4000 rpm for 5 min, to remove impurities and lipids in the plasma. Measured the value of pH, if required, adjusted it to 7.4±0.1.
    2.2 Prepared 400 μM intermediate solution by diluting 4 μL of the working solution (10 mM) with 96 μL DMSO.
    2.3 Preparation of incubation samples: Remove 3 μL of intermediate solution (400 μM) to mix with 597 μL of blank plasma to achieve 2 μM of final concentration. Incubate each time point samples (0 min, 10 min, 30 min, 60 min, 120 min, in duplicate) at 37° C. in water bath.
    2.4 An aliquot of 100 μL samples of the final spiked plasma for each time point were removed to sample collected plates, added 400 μL of stop solution (200 ng/mL Tolbutamide plus 20 ng/mL Buspirone in 50% ACN/MeOH) to precipitate protein. Mixed thoroughly.
    2.5 Centrifuged each plate at 4,000 rpm for 20 min. Transfered an aliquot of supernatant (100 μL) from each well to sample plate and mixed with 200 μL ultra pure water. Shaked the plate at 800 rpm for about 10 min before submitting to LC-MS/MS analysis.

3. Experimental Data Analysis
    The ratio of the peak area to the internal standard peak area was used to assess the decrease of the test compound to be measured. The % remaining of the test compound after incubation in plasma was calculated using following equation:

% Remaining=100×(PAR at appointed incubation time/PAR at T0 time)

wherein PAR is the peak area ratio of analyte versus internal standard (IS)
    The appointed incubation time points are: 0 min, 10 min, 30 min, 60 min, 120 min; T0: Samples prior to incubation.

4. Stability of Compounds in Rat and Human Plasma
The experimental results are shown in Table 5:

TABLE 5

Evaluation of the Stability of each test compound in rat and human plasma

| Test Compounds | Species | Time (min) | Recovery (%) |
|---|---|---|---|
| (−)-Lesinurad | Human Plasma | 0 | 100.0 |
| | | 10 | 100.3 |
| | | 30 | 100.4 |
| | | 60 | 99.6 |
| | | 120 | 101.0 |
| | SD Rat Plasma | 0 | 100.0 |
| | | 10 | 101.6 |
| | | 30 | 99.9 |
| | | 60 | 97.9 |
| | | 120 | 100.3 |
| (+)-Lesinurad | Human Plasma | 0 | 100.0 |
| | | 10 | 100.2 |
| | | 30 | 99.5 |
| | | 60 | 99.4 |
| | | 120 | 100.4 |
| | SD Rat Plasma | 0 | 100.0 |
| | | 10 | 99.5 |
| | | 30 | 100.3 |
| | | 60 | 99.7 |
| | | 120 | 101.2 |
| EUCA | Human Plasma | 0 | 100.0 |
| | | 10 | 49.9 |
| | | 30 | 20.7 |
| | | 60 | 7.1 |
| | | 120 | 1.8 |

TABLE 5-continued

Evaluation of the Stability of each test compound in rat and human plasma

| Test Compounds | Species | Time (min) | Recovery (%) |
|---|---|---|---|
| ENAL | SD Rat Plasma | 0 | 100.0 |
| | | 10 | 63.0 |
| | | 30 | 19.3 |
| | | 60 | 3.0 |
| | | 120 | 0.0 |

Note:
The % remaining of test compound after incubation in plasma was calculated using following equation: % Remaining = 100 × (PAR at appointed incubation time/PAR at T0 time) wherein PAR is the peak area ratio of analyte versus internal standard (IS)

The experimental data showed that (+)-Lesinurad and (−)-Lesinurad were very stable after co-incubation with SD-rat plasma and human plasma for 2 hours.

Test 6: In Vivo Pharmacokinetic Study of the Test Compounds in Rats

1. Experimental Objective

The purpose of this study was to determine the pharmacokinetics of compounds in male Sprague-Dawley rats following a single intravenous bolus and oral gavage administration of (+)-Lesinurad, (−)-Lesinurad and (±)-Lesinurad, respectively. To study the pharmacokinetic behavior of the compounds in rats and to evaluate their pharmacokinetic characteristics, their concentrations in plasma were determined by LC/MS/MS.

2. Experimental Scheme 2.1 Experimental Chemicals (+)-Lesinurad, (−)-Lesinurad and (±)-Lesinurad 2.2 Experimental Animals 18 adult male SD rats were divided into 6 groups (each with compound IV, PO group), 3 rats in each group, purchased from Shanghai SIPPR/BK experimental animal Co. Ltd., animal production license number: SCXK (Shanghai) 2013-0016.

2.3 Test chemical Formulations

Appropriate amount of sample was added to a certain amount of pure water, the pH were adjusted to 7-8, to prepare to be 1 mg/mL (filtered and clarified) and 2 mg/mL (with a few particles of suspension) for IV and PO administration.

2.4 Administration 18 male SD rats were randomly assigned to 6 treatment groups, 3 rats in each group. Male rats were administrated IV and PO respectively after fasting overnight. The IV dosage was 2 mg/kg, the dose volume was 2 mL/kg, the PO dosage was 10 mg/kg, and the dose volume was 5 mL/kg.

3. Experimental Procedure

For IV group, 250 µL blood samples were collected before administration, and 0.083, 0.25, 0.5, 1, 2, 4, 8, 24 hours after administration, and placed in K2-EDTA anticoagulant tube, centrifuged at 3000 rpm for 15 minutes, plasma was separated, stored at −80° C. For PO Group, blood samples were collected before administration, and 0.25, 0.5, 1, 2, 4, 8, 24 hours after administration, and the other operations were the same as group IV. The content of the test compounds in the plasma of rats after administration of IV and PO were determined by LC/MS/MS method. The linear range of the assay was 6.00-18000 nM, and the lower limit of quantification was 6 nM; the plasma samples were analyzed by pretreatment with precipitated proteins.

4. Results of Pharmacokinetic Parameters

The experimental results was shown in Table 6:

TABLE 6

Pharmacokinetic Parameters of Each Test Compound in Rats

| | Test compounds | (±)-Lesinurad | (+)-Lesinurad | (−)-Lesinurad |
|---|---|---|---|---|
| IV (2 mpk) | $C_0$ (nM) | 11611.63 ± 1984.94 | 11504.99 ± 2718.15 | 9385.69 ± 3214.15 |
| | $T_{1/2}$ (h) | 1.80 ± 0.65 | 1.61 ± 0.11 | 1.46 ± 0.03 |
| | Vdss (L/kg) | 0.76 ± 0.29 | 0.69 ± 0.03 | 0.75 ± 0.10 |
| | Cl (mL/min/kg) | 5.72 ± 1.09 | 5.50 ± 0.36 | 5.76 ± 0.59 |
| | $AUC_{0-inf}$ (nM · h) | 14823.49 ± 3149.73 | 15039.02 ± 1026.80 | 14419 ± 1546.95 |
| | $MRT_{0-inf}$ (h) | 2.21 ± 0.63 | 2.08 ± 0.08 | 2.16 ± 0.07 |
| PO (10 mpk) | $C_{max}$ (nM) | 14496.67 ± 8465.93 | 7760.00 ± 5146.10 | 10976.67 ± 3986.43 |
| | $T_{max}$ (h) | 2.33 ± 1.53 | 3.00 ± 1.73 | 2.33 ± 1.53 |
| | $T_{1/2}$ (h) | 2.46 ± 0.18 | 2.25 ± 0.02 | 2.17 ± 0.10 |
| | $AUC_{0-inf}$ (nM · h) | 62491.15 ± 12086.78 | 32684.73 ± 13432.35 | 46943.91 ± 11498.70 |
| | $MRT_{0-inf}$ (h) | 4.63 ± 1.16 | 4.09 ± 0.87 | 3.92 ± 0.64 |
| | Bioavailability (%) | 84.35 | 44.65 | 65.11 |

The experimental results showed that (+)-Lesinurad and (−)-Lesinurad behaved similar in SD-rats, as well as (±)-Lesinurad. For the two atropisomers, no transformation was observed in vivo. (+)-Lesinurad and (−)-Lesinurad remained as single atropisomer in the circumstance system.

What is claimed is:

1. A laevorotary or dextrogyrate compound of formula (I), or a pharmaceutically acceptable salt thereof, in the form of a single axially chiral isomer or enriched in an axially chiral isomer

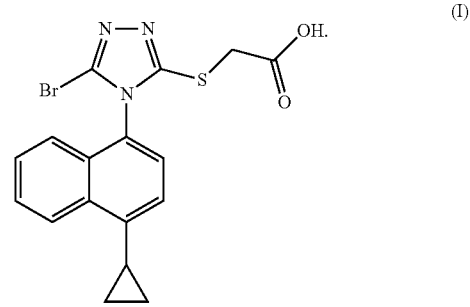 [SMILES: O=C(O)CSc1nnc(Br)n1-c1ccc(C2CC2)c2ccccc12]

(I)

2. A compound of formula (II) or formula (III), or a pharmaceutically acceptable salt thereof:

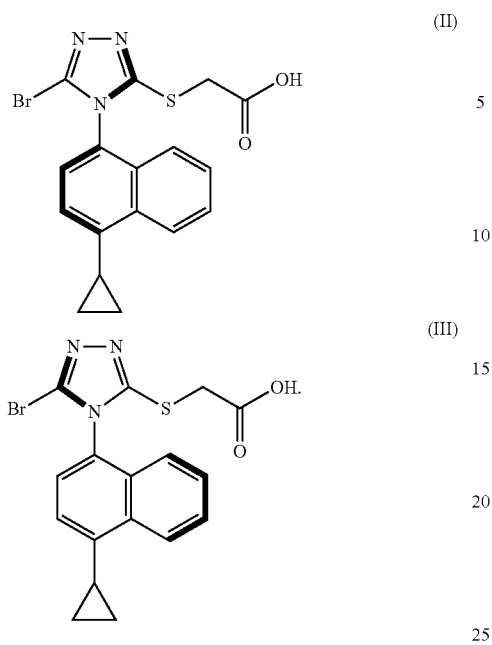

3. A process for the preparation of a compound according to claim 1, which comprises the synthetic route of formula (IV):

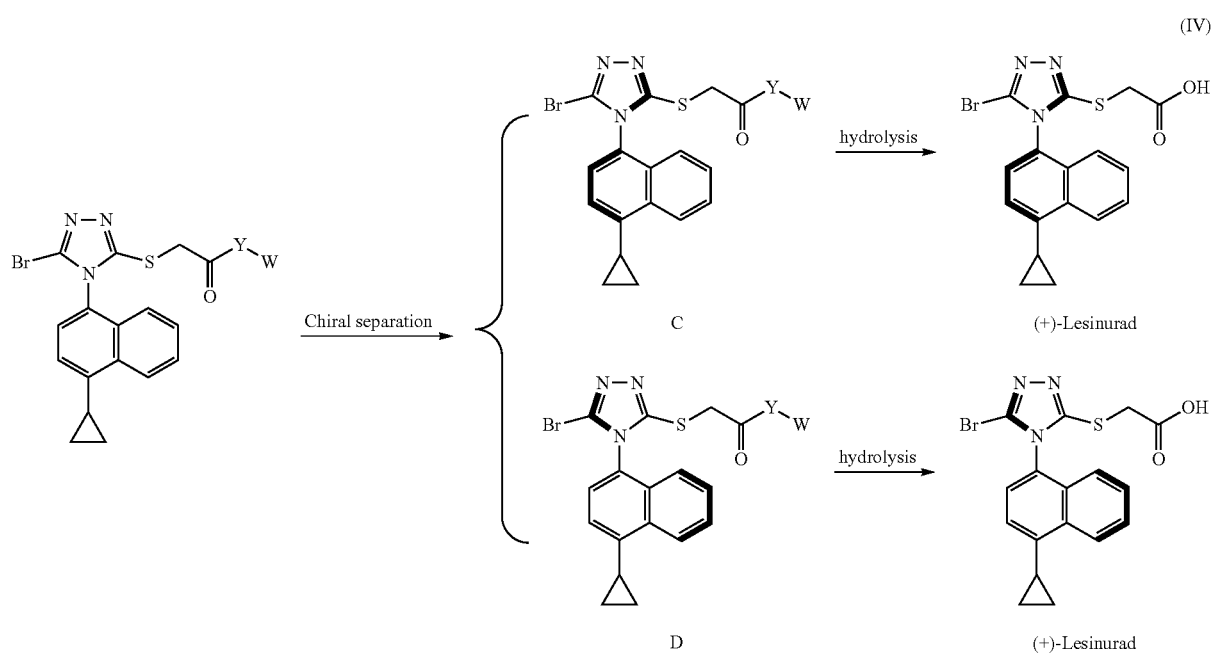

wherein,

Y is selected from O, NH or N (W); W is selected from the group consisting of an alkyl, a heteroalkyl, an aralkyl, a heteroarylalkyl, an aryl, a heteroaryl, and said alkyl, heteroalkyl, aralkyl, heteroarylalkyl, aryl, and heteroaryl substituted by 1 or 2 or 3 of halogen, OH, CN or $NH_2$; chiral separation refers to SFC separation.

4. A process for the preparation of a compound according to claim 1, which comprises the synthetic route of formula (V):

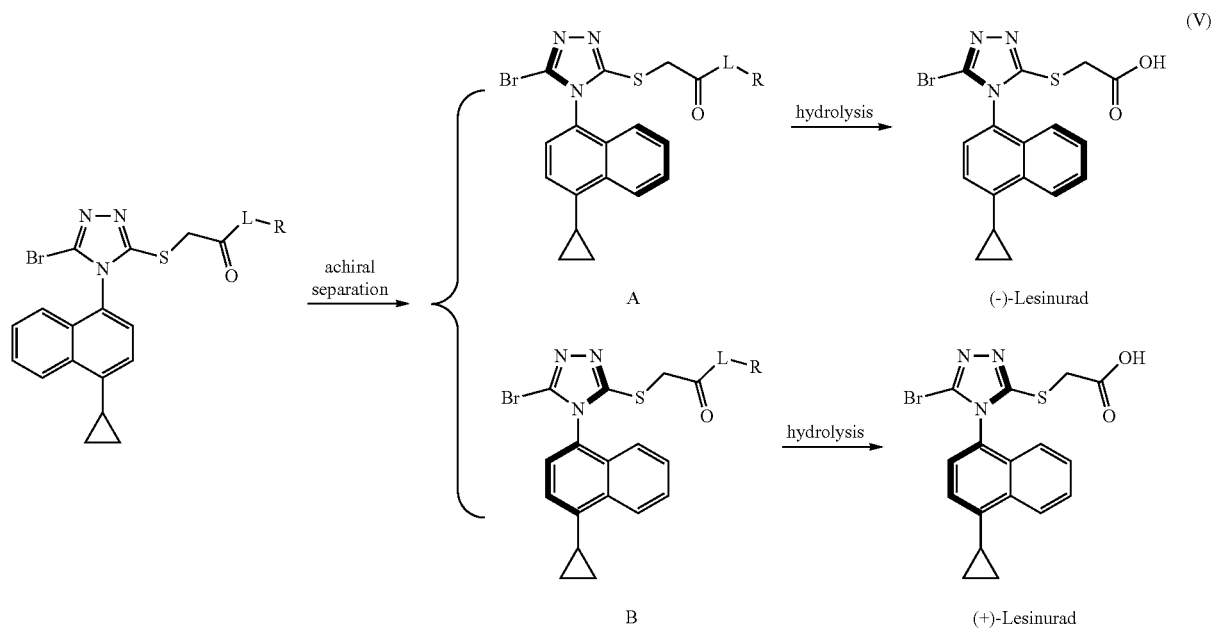

wherein, L is selected from O, NH or N (R);

R represents a chiral group selected from the group consisting of a chiral alkyl, a chiral heteroalkyl, a chiral aralkyl, a chiral heteroaralkyl, a chiral aryl, a chiral heteroaryl and said chiral alkyl, chiral heteroalkyl, chiral aralkyl, chiral heteroaralkyl, chiral aryl, and chiral heteroaryl substituted by 1 or 2 or 3 of halogen, OH, CN or NH₂;

achiral separation refers to recrystallization, thin-layer chromatography separation, column chromatography separation, rapid column separation, and separation using preparative chromatographic columns of achiral fillers.

5. The process according to claim 4, which comprises the synthetic route of formula (VI):

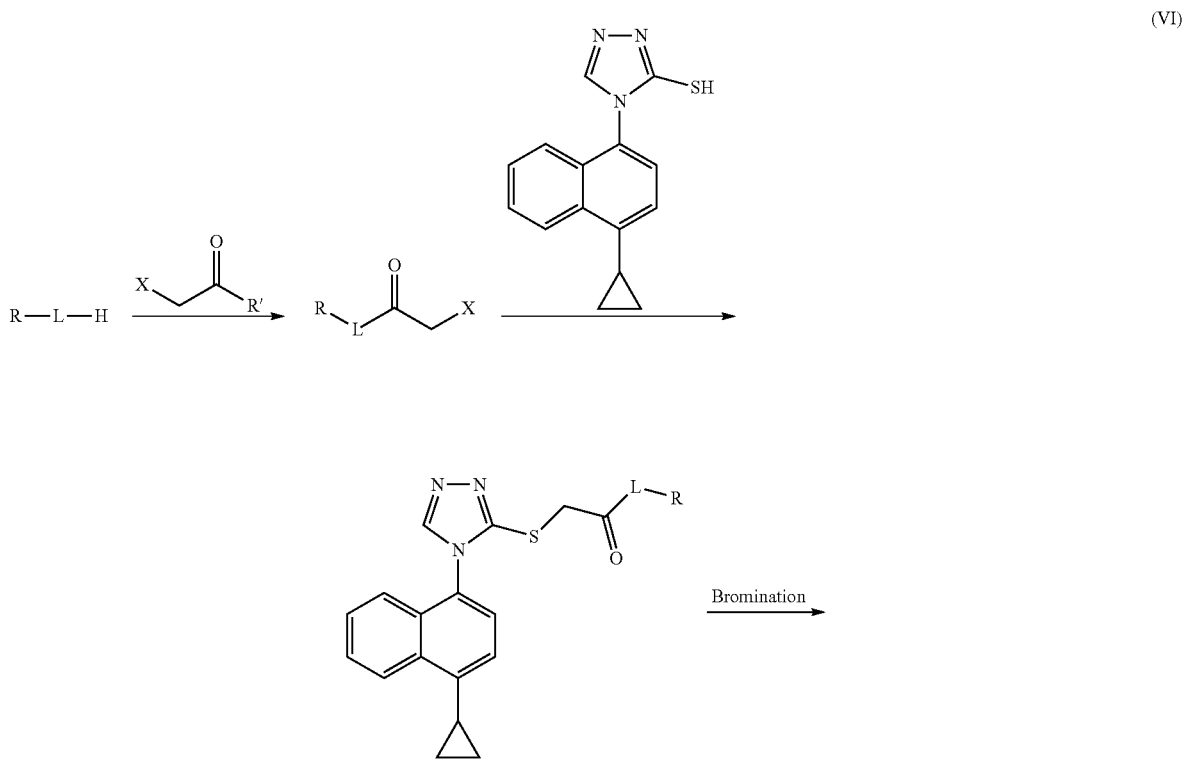

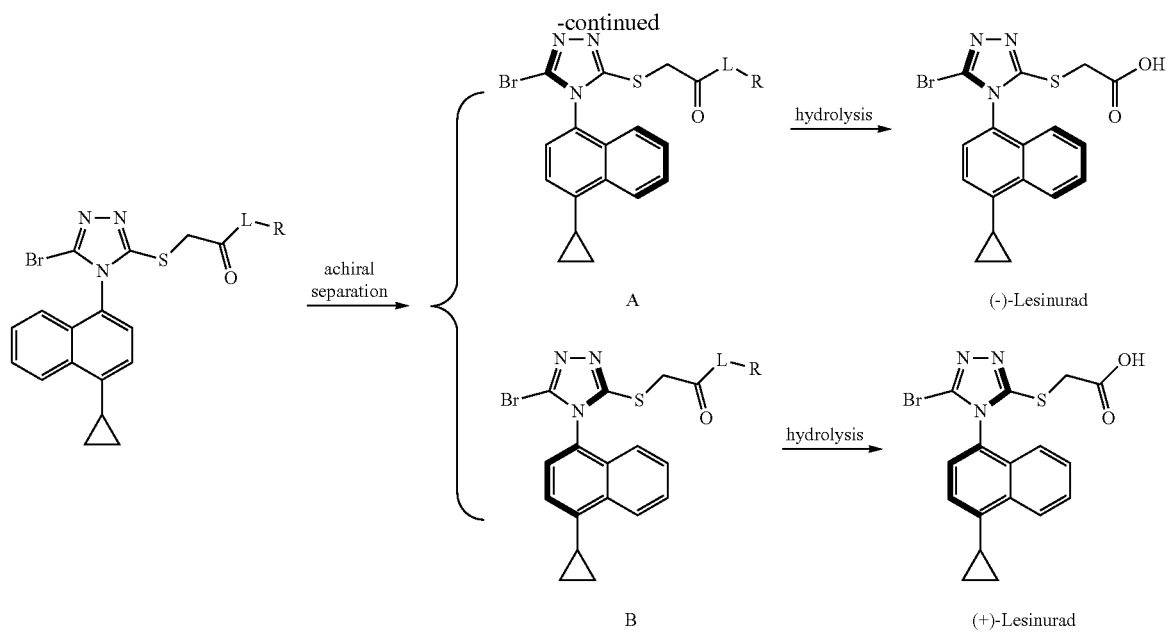

(-)-Lesinurad (+)-Lesinurad wherein, X is selected from the group consisting of F, Cl, Br, I, and sulfonate; R' is selected from the group consisting of F, Cl, Br, I and OH.

6. The process according to claim 3, wherein the hydrolysis is carried out under strong base conditions; wherein the strong base is LiOH, NaOH, or KOH.

7. The process according to claim 4, wherein, R is selected from the group consisting of

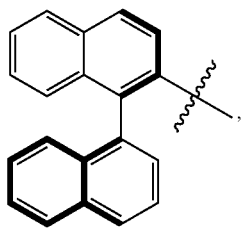

phenylalkyl and phenylalkyl wherein a carbon atom of the alkyl group of the phenylalkyl is substituted by one or more of N, O, S, C(=O), C(=O)O, S(=O), S(=O)$_2$, C(=O)NH, S(=O)NH, S(=O)$_2$NH or NHBoc.

8. The process according to claim 5, wherein, the brominating reagent is Br$_2$/base; wherein the base is selected from pyridine, triethylamine, or DIPEA.

9. The process according to claim 5, wherein, the sulfonate is selected from the group consisting of mesylate, p-toluenesulfonate, p-nitrobenzenesulfonate and trifluoromethanesulfonate.

10. A pharmaceutical composition comprising a therapeutically effective amount of a compound or a pharmaceutically acceptable salt thereof according to claim 1, as an active ingredient and a pharmaceutically acceptable carrier.

11. A process for treating a patient in need of a medicament for a condition associated with abnormal serum uric acid level, comprising administering to the patient an effective amount of a compound or a pharmaceutically acceptable salt thereof according to claim 1.

12. The process according to claim 3, wherein W is C$_{1-6}$ alkyl or said C$_{1-6}$ alkyl substituted by 1 or 2 or 3 of halogen, OH, CN and NH$_2$.

13. The process according to claim 7 wherein R is selected from the group consisting of

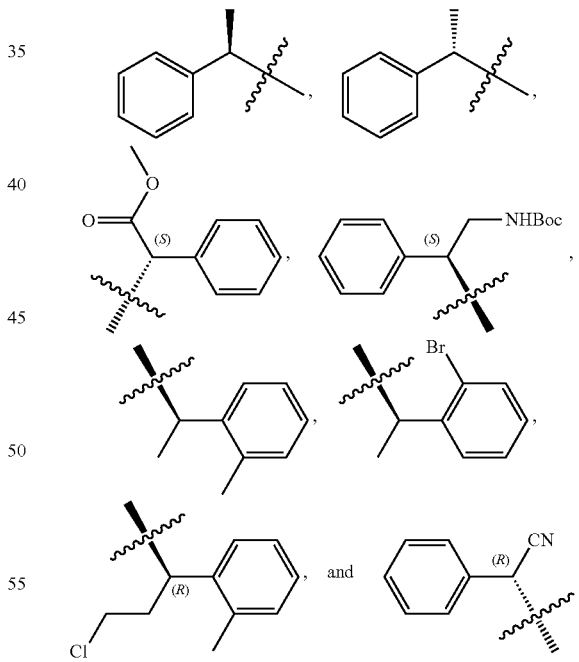

14. The process according to claim 4, wherein the hydrolysis is carried out under strong base conditions wherein the strong base is selected from the group consisting of LiOH, NaOH, and KOH.

15. The process according to claim 5, wherein the hydrolysis is carried out under strong base conditions wherein the strong base is selected from the group consisting of LiOH, NaOH, and KOH.

16. The process according to claim 5 wherein, R is selected from the group consisting of

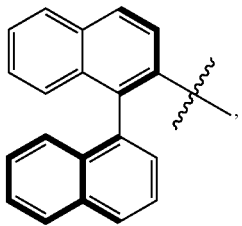

phenylalkyl and phenylalkyl wherein a carbon atom of the alkyl group of the phenylalkyl is substituted by one or more of N, O, S, C(=O), C(=O)O, S(=O), S(=O)$_2$, C(=O)NH, S(=O)NH, S(=O)$_2$NH or NHBoc.

17. The process according to claim 16 wherein R is selected from the group consisting of

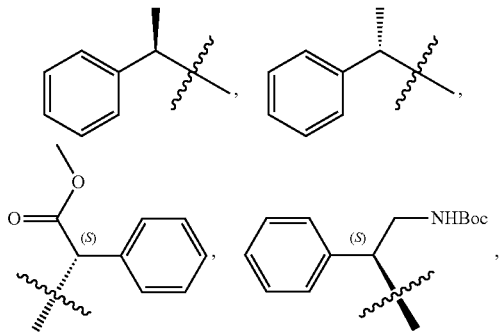

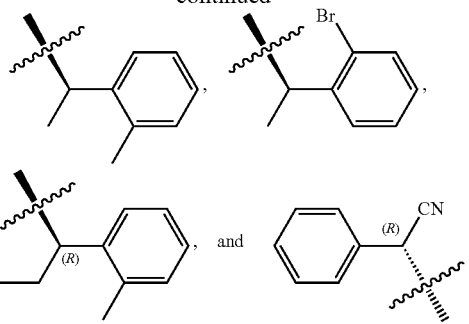

18. A pharmaceutical composition comprising a therapeutically effective amount of a compound or a pharmaceutically acceptable salt thereof according to claim 2, as an active ingredient and a pharmaceutically acceptable carrier.

19. A process for treating a patient in need of a medicament for a condition associated with abnormal serum uric acid level, comprising administering to the patient a medicament comprising an effective amount of a compound or a pharmaceutically acceptable salt thereof according to claim 2.

20. A process for treating a patient in need of a medicament for a condition associated with abnormal serum uric acid level, comprising administering to the patient a medicament comprising an effective amount of a pharmaceutical composition according to claim 10.

* * * * *